US010696954B2

United States Patent
Kohler et al.

(10) Patent No.: US 10,696,954 B2
(45) Date of Patent: Jun. 30, 2020

(54) HYBRID PEROXIDASES WITH ENHANCED ACTIVITY AND STABILITY

(71) Applicants: The Regents of the University of California, Oakland, CA (US); National Technology & Engineering Solutions of Sandia, LLC (NTESS), Albuquerque, NM (US)

(72) Inventors: Amanda C. Kohler, Albany, CA (US); Kenneth L. Sale, Livermore, CA (US); Blake A. Simmons, San Francisco, CA (US)

(73) Assignees: The Regents of the University of California, Oakland, CA (US); National Technology & Engineering Solutions of Sandia, LLC, Albuquerque, NM (US)

( * ) Notice: Subject to any disclaimer, the term of this patent is extended or adjusted under 35 U.S.C. 154(b) by 0 days.

(21) Appl. No.: 16/215,479

(22) Filed: Dec. 10, 2018

(65) Prior Publication Data
US 2019/0241875 A1    Aug. 8, 2019

Related U.S. Application Data

(60) Provisional application No. 62/596,728, filed on Dec. 8, 2017.

(51) Int. Cl.
| | | |
|---|---|---|
| *C12N 9/02* | (2006.01) | |
| *C12N 9/08* | (2006.01) | |
| *C12P 3/00* | (2006.01) | |

(52) U.S. Cl.
CPC .............. *C12N 9/0065* (2013.01); *C12P 3/00* (2013.01); *C12Y 111/01007* (2013.01)

(58) Field of Classification Search
CPC .................................................... C12Y 111/00
USPC ................................................. 435/168, 189
See application file for complete search history.

(56) References Cited

U.S. PATENT DOCUMENTS

2013/0302878 A1\* 11/2013 Oestergaard ........ C12N 9/0065
435/192

OTHER PUBLICATIONS

Rodriguez-Lopez, et al., "Mechanism of Reaction of Hydrogen Peroxide with Horseradish Peroxidase: Identification of Intermediates in the Catalytic Cycle," J. Am. Chem. Soc. 2001, vol. 123, No. 48, pp. 11838-11847.
Morales, et al., "Two Oxidation Sites for Low Redox Potential Substrates," The Journal of Biological Chemistry, 2012, vol. 287, No. 49, pp. 41053-41067.
Saez-Jimenez, et al., "Unveiling the basis of alkaline stability of an evolved versatile peroxidase," Biochem. J., 2016, vol. 473, pp. 1917-1928.
Fernandez-Fueyo, et al., "Engineering a fungal peroxidase that degrades lignin at very acidic pH," Biotechnology for Biofuels, 2014, 7:114, pp. 1-12.
Ruiz-Duenas, et al., "Substrate oxidation sites in versatile peroxidase and other basidiomycete peroxidases," Journal of Experimental Botany, 2009, vol. 60, No. 2, pp. 441-452.
Watanabe, et al., "Crystal structure and statistical coupling analysis of highly glycosylated peroxidase from royal palm tree (*Roystonea regia*),"Journal of Structural Biology, 2010, vol. 169, pp. 226-242.
Knop, et al., "Limits of Versatility of Versatile Peroxidase," Applied and Environmental Microbiology, 2016, vol. 82, No. 14, pp. 4070-4080.
Zamorano, et al., "Thermodynamic characterization of the palm tree *Roystonea regia* peroxidase stability," Biochimie 2008, vol. 90, pp. 1737-1749.

\* cited by examiner

*Primary Examiner* — Tekchand Saidha
(74) *Attorney, Agent, or Firm* — Kilpatrick Townsend & Stockton LLP

(57) ABSTRACT

Described herein are stable hybrid peroxidases capable of oxidizing manganese and high-reduction potential substrates, methods of generating such peroxidases, and method of using the peroxidases in reactions that are less environmentally toxic.

13 Claims, 11 Drawing Sheets

Specification includes a Sequence Listing.

SEQUENCE LISTING

<160> NUMBER OF SEQ ID NOS: 10

<210> SEQ ID NO 1
<211> LENGTH: 304
<212> TYPE: PRT
<213> ORGANISM: Roystonea regia

<400> SEQUENCE: 1

```
Asp Leu Gln Ile Gly Phe Tyr Asn Thr Ser Cys Pro Thr Ala Glu Ser
1               5                   10                  15

Leu Val Gln Gln Ala Val Ala Ala Phe Ala Asn Asn Ser Gly Ile
            20                  25                  30

Ala Pro Gly Leu Ile Arg Met His Phe His Asp Cys Phe Val Arg Gly
        35                  40                  45

Cys Asp Ala Ser Val Leu Leu Asp Ser Thr Ala Asn Asn Thr Ala Glu
    50                  55                  60

Lys Asp Ala Ile Pro Asn Asn Pro Ser Leu Arg Gly Phe Glu Val Ile
65                  70                  75                  80

Thr Ala Ala Lys Ser Ala Val Glu Ala Ala Cys Pro Gln Thr Val Ser
                85                  90                  95

Cys Ala Asp Ile Leu Ala Phe Ala Ala Arg Asp Ser Ala Asn Leu Ala
                100                 105                 110

Gly Asn Ile Thr Tyr Gln Val Pro Ser Gly Arg Arg Asp Gly Thr Val
            115                 120                 125

Ser Leu Ala Ser Glu Ala Asn Ala Gln Ile Pro Ser Pro Leu Phe Asn
130                 135                 140

Ala Thr Gln Leu Ile Asn Ser Phe Ala Asn Lys Thr Leu Thr Ala Asp
145                 150                 155                 160

Glu Met Val Thr Leu Ser Gly Ala His Ser Ile Gly Val Ala His Cys
                165                 170                 175

Ser Ser Phe Thr Asn Arg Leu Tyr Asn Phe Asn Ser Gly Ser Gly Ile
                180                 185                 190

Asp Pro Thr Leu Ser Pro Ser Tyr Ala Ala Leu Leu Arg Asn Thr Cys
            195                 200                 205

Pro Ala Asn Ser Thr Arg Phe Thr Pro Ile Thr Val Ser Leu Asp Ile
    210                 215                 220

Ile Thr Pro Ser Val Leu Asp Asn Met Tyr Tyr Thr Gly Val Gln Leu
225                 230                 235                 240

Thr Leu Gly Leu Leu Thr Ser Asp Gln Ala Leu Val Thr Glu Ala Asn
                245                 250                 255

Leu Ser Ala Ala Val Lys Ala Asn Ala Met Asn Leu Thr Ala Trp Ala
            260                 265                 270

Ser Lys Phe Ala Gln Ala Met Val Lys Met Gly Gln Ile Glu Val Leu
        275                 280                 285

Thr Gly Thr Gln Gly Glu Ile Arg Thr Asn Cys Ser Val Val Asn Ser
    290                 295                 300
```

<210> SEQ ID NO 2
<211> LENGTH: 332
<212> TYPE: PRT
<213> ORGANISM: Pleurotus ostreatus

<400> SEQUENCE: 2

```
Met Ala Thr Cys Ala Asp Gly Arg Thr Thr Ala Asn Ala Ala Cys Cys
1               5                   10                  15

Val Leu Phe Pro Ile Leu Asp Asp Ile Gln Glu Asn Leu Phe Asp Gly
```

```
            20                  25                  30

Ala Gln Cys Gly Glu Glu Val His Glu Ser Leu Arg Leu Thr Phe His
            35                  40                  45

Asp Ala Ile Gly Phe Ser Pro Thr Leu Gly Gly Gly Ala Asp Gly
            50                  55                  60

Ser Ile Ile Thr Phe Asp Thr Ile Glu Thr Asn Phe Pro Ala Asn Ala
 65                  70                  75                  80

Gly Ile Asp Glu Ile Val Ser Ala Gln Lys Pro Phe Val Ala Lys His
                 85                  90                  95

Asn Ile Ser Ala Gly Asp Phe Ile Gln Phe Ala Gly Ala Val Gly Val
                100                 105                 110

Ser Asn Cys Pro Gly Gly Val Arg Ile Pro Phe Phe Leu Gly Arg Pro
            115                 120                 125

Asp Ala Val Ala Ala Ser Pro Asp His Leu Val Pro Glu Pro Phe Asp
            130                 135                 140

Ser Val Asp Thr Ile Leu Ala Arg Met Gly Asp Ala Gly Phe Ser Ala
145                 150                 155                 160

Val Glu Val Val Trp Leu Leu Ala Ser His Ser Ile Ala Ala Ala Asp
                165                 170                 175

Lys Val Asp Pro Ser Ile Pro Gly Thr Pro Phe Asp Ser Thr Pro Gly
            180                 185                 190

Val Phe Asp Ser Gln Phe Phe Ile Glu Thr Gln Leu Lys Gly Arg Leu
            195                 200                 205

Phe Pro Gly Thr Pro Asp Asn Lys Gly Glu Val Gln Ser Pro Leu Gln
        210                 215                 220

Gly Glu Ile Arg Leu Gln Ser Asp His Leu Leu Ala Arg Asp Pro Gln
225                 230                 235                 240

Thr Ala Cys Glu Trp Gln Ser Met Val Asn Asn Gln Pro Lys Ile Gln
                245                 250                 255

Asn Arg Phe Ala Gly Thr Met Ser Lys Met Ala Leu Leu Gly Gln Asp
            260                 265                 270

Lys Ser Lys Leu Ile Asp Cys Ser Asp Ile Ile Pro Thr Pro Pro Ala
        275                 280                 285

Leu Val Gly Ala Ala His Leu Pro Ala Gly Phe Ser Leu Ser Asp Val
            290                 295                 300

Glu Gln Ala Cys Ala Glu Thr Pro Phe Pro Ala Leu Thr Ala Asp Pro
305                 310                 315                 320

Gly Pro Val Thr Ser Val Pro Pro Val Pro Gly Ser
                325                 330

<210> SEQ ID NO 3
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Leu Gln Ile Gly Phe Tyr Asn Thr Ser Cys Pro Thr Ala Glu Ser
 1                   5                  10                  15

Leu Val Gln Gln Ala Val Ala Ala Phe Ala Asn Ala Ser Glu Ile
            20                  25                  30

Ala Pro Glu Leu Ile Arg Met His Phe His Asp Cys Phe Val Arg Gly
            35                  40                  45
```

```
Cys Asp Ala Ser Val Leu Leu Asp Ser Thr Ala Asn Asn Thr Ala Glu
 50                  55                  60
Lys Asp Ala Ile Pro Asn Asn Pro Ser Leu Ala Gly Phe Glu Val Ile
 65                  70                  75                  80
Thr Ala Ala Lys Ser Ala Val Glu Ala Ala Cys Pro Gln Thr Val Ser
                 85                  90                  95
Cys Ala Asp Ile Leu Ala Phe Ala Ala Arg Asp Ser Ala Asn Leu Ala
            100                 105                 110
Gly Asn Ile Thr Tyr Gln Val Pro Ser Gly Arg Arg Asp Gly Thr Val
            115                 120                 125
Ser Leu Ala Ser Glu Ala Asn Ala Gln Ile Pro Glu Pro Phe Asp Asn
130                 135                 140
Ala Thr Gln Leu Ile Asn Ser Met Ala Asn Lys Thr Leu Thr Ala Asp
145                 150                 155                 160
Glu Met Val Trp Leu Ser Gly Ala His Ser Ile Gly Asp Ala His Cys
                165                 170                 175
Ser Ser Phe Thr Asn Arg Leu Tyr Asn Phe Asn Ser Gly Ser Gly Ile
            180                 185                 190
Asp Pro Thr Leu Ser Pro Ser Tyr Ala Ala Leu Leu Arg Asn Thr Cys
            195                 200                 205
Pro Ala Asn Ser Thr Arg Phe Thr Pro Ile Thr Val Ser Phe Asp Ile
210                 215                 220
Ile Thr Pro Ser Val Leu Asp Asn Met Tyr Tyr Thr Gly Val Gln Leu
225                 230                 235                 240
Thr Leu Gly Leu Leu Thr Ser Asp Gln Ala Leu Val Thr Glu Ala Asn
                245                 250                 255
Leu Ser Ala Glu Val Lys Ala Met Ala Met Asn Leu Thr Lys Trp Ala
            260                 265                 270
Ser Arg Phe Ala Gln Thr Met Val Lys Met Gly Gln Ile Glu Val Leu
            275                 280                 285
Thr Gly Thr Gln Gly Glu Ile Arg Thr Asn Cys Ser Val Val Asn Ser
            290                 295                 300

<210> SEQ ID NO 4
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Gly Ser Ser His His His His His His Ser Ser Gly Leu Val Pro
 1               5                  10                  15

Arg Gly Ser His Met Ala Ser
            20

<210> SEQ ID NO 5
<211> LENGTH: 303
<212> TYPE: PRT
<213> ORGANISM: Chamaerops excelsa

<400> SEQUENCE: 5

Asp Leu Gln Ile Gly Phe Tyr Asn Gln Ser Cys Pro Ser Ala Glu Ser
 1               5                  10                  15

Leu Val Gln Gln Gly Val Ala Ala Phe Ala Asn Asn Ser Gly Ile
                20                  25                  30
```

```
Ala Pro Gly Leu Ile Arg Met His Phe His Asp Cys Phe Val Arg Gly
         35                  40                  45

Cys Asp Gly Ser Val Leu Leu Asp Ser Thr Asp Thr Asn Thr Ala Glu
 50                  55                  60

Lys Asp Ala Ala Pro Asn Asn Pro Ser Leu Arg Gly Phe Glu Val Ile
 65                  70                  75                  80

Ala Ala Ala Lys Ser Ala Val Glu Ala Ala Cys Pro Lys Thr Val Ser
                 85                  90                  95

Cys Ala Asp Ile Leu Ala Phe Ala Ala Arg Asp Ser Ala Ala Leu Ala
             100                 105                 110

Gly Asn Ile Thr Tyr Gln Val Pro Ser Gly Arg Arg Asp Gly Asn Val
         115                 120                 125

Ser Leu Ala Ser Glu Ala Leu Thr Asn Ile Pro Ala Pro Thr Phe Asn
 130                 135                 140

Ala Thr Gln Leu Ile Asn Ser Phe Ala Gly Lys Asn Leu Thr Ala Asp
 145                 150                 155                 160

Glu Met Val Thr Leu Ser Gly Ala His Ser Ile Gly Val Ser His Cys
                 165                 170                 175

Phe Ser Phe Leu Asn Arg Ile Tyr Asn Phe Ser Asn Thr Ser Gln Val
             180                 185                 190

Asp Pro Thr Leu Ser Ser Ser Tyr Ala Asp Leu Leu Arg Thr Lys Cys
         195                 200                 205

Pro Ser Asn Ser Thr Arg Phe Thr Pro Ile Thr Val Ser Leu Asp Ile
 210                 215                 220

Ile Thr Pro Thr Val Leu Asp Asn Arg Tyr Tyr Thr Gly Val Gln Leu
225                 230                 235                 240

Thr Leu Gly Leu Leu Thr Ser Asp Gln Ala Leu Val Thr Glu Ala Asn
                 245                 250                 255

Leu Ser Ala Ala Val Lys Asn Asn Ala Asp Asn Leu Thr Ala Trp Val
             260                 265                 270

Ala Glu Phe Ala Gln Ala Ile Val Lys Met Gly Gln Ile Glu Val Leu
         275                 280                 285

Thr Gly Thr Gln Gly Glu Ile Arg Thr Asn Cys Ser Val Val Asn
 290                 295                 300

<210> SEQ ID NO 6
<211> LENGTH: 306
<212> TYPE: PRT
<213> ORGANISM: Elaeis guieensis

<400> SEQUENCE: 6

Asp Leu Gln Ile Gly Phe Tyr Asn Thr Ser Cys Pro Thr Ala Glu Ser
1               5                   10                  15

Leu Val Gln Gln Ala Val Ala Ala Phe Ala Asn Asn Ser Gly Ile
                 20                  25                  30

Ala Ala Gly Leu Ile Arg Leu His Phe His Asp Cys Phe Val Arg Gly
             35                  40                  45

Cys Asp Ala Ser Val Leu Leu Asp Ser Thr Ala Asn Asn Thr Ala Glu
 50                  55                  60

Lys Asp Ala Pro Pro Asn Asn Pro Ser Leu Arg Gly Phe Glu Val Ile
 65                  70                  75                  80

Ala Ala Ala Lys Ser Ala Val Glu Ala Ala Cys Pro Lys Thr Val Ser
                 85                  90                  95

Cys Ala Asp Ile Val Ala Phe Ala Ala Arg Asp Ser Ala Thr Leu Ala
             100                 105                 110
```

```
Gly Asn Ile Ser Tyr Gln Val Pro Ser Gly Arg Arg Asp Gly Asn Val
            115                 120                 125

Ser Leu Ala Ser Glu Ala Asn Ala Asn Ile Pro Ser Pro Leu Phe Asn
    130                 135                 140

Ala Thr Gln Leu Ile Asn Ser Phe Ala Gly Lys Asn Leu Thr Thr Asp
145                 150                 155                 160

Glu Met Val Thr Leu Ser Gly Ala His Ser Ile Gly Val Ala His Cys
                165                 170                 175

Ser Ser Phe Leu Asn Arg Ile Tyr Asn Phe Ser Asn Thr Ser Asp Val
            180                 185                 190

Asp Pro Thr Leu Ser Ser Ala Tyr Ala Asp Leu Leu Lys Asn Lys Cys
        195                 200                 205

Pro Ser Asn Ser Thr Arg Phe Thr Pro Ile Thr Val Ser Leu Asp Ile
    210                 215                 220

Ile Thr Pro Thr Val Leu Asp Asn Arg Tyr Tyr Thr Gly Val Glu Leu
225                 230                 235                 240

Thr Leu Gly Leu Leu Thr Ser Asp Gln Ala Leu Val Thr Glu Ala Asn
                245                 250                 255

Leu Ser Ala Ala Val Gln Asp Asn Ala Asn Asn Ser Ala Thr Trp Ala
            260                 265                 270

Ser Lys Phe Ala Gln Ala Met Val Lys Met Gly Leu Ile Glu Val Leu
        275                 280                 285

Thr Gly Thr Gln Gly Glu Ile Arg Thr Asn Cys Ser Val Val Asn Ser
    290                 295                 300

Ala Ser
305

<210> SEQ ID NO 7
<211> LENGTH: 344
<212> TYPE: PRT
<213> ORGANISM: Trachycarpus fortunei

<400> SEQUENCE: 7

Met Ser Arg Pro Val Lys Leu Phe Phe Leu Ala Phe Leu Ala Leu Leu
1               5                   10                  15

Ala Ala Val His Gly Asp Leu Gln Ile Gly Phe Tyr Asn Gln Ser Cys
            20                  25                  30

Pro Ser Ala Glu Ser Leu Val Gln Gln Ala Val Ala Ala Ala Phe Ala
        35                  40                  45

Asn Asn Ser Gly Ile Ala Pro Gly Leu Ile Arg Met His Phe His Asp
    50                  55                  60

Cys Phe Val Arg Gly Cys Asp Ala Ser Val Leu Leu Asp Ser Thr Ala
65                  70                  75                  80

Asn Asn Thr Ala Glu Lys Asp Ala Ala Pro Asn Asn Pro Ser Leu Arg
                85                  90                  95

Gly Phe Glu Val Ile Ala Ala Lys Ser Ala Val Glu Ala Ala Cys
            100                 105                 110

Pro Lys Thr Val Ser Cys Ala Asp Ile Leu Ala Phe Ala Ala Arg Asp
        115                 120                 125

Ser Ala Ala Leu Ala Gly Asn Ile Thr Tyr Gln Val Pro Ser Gly Arg
    130                 135                 140

Arg Asp Gly Asn Val Ser Leu Ala Ser Glu Ala Leu Thr Asn Ile Pro
145                 150                 155                 160

Ala Pro Thr Phe Asn Ala Thr Gln Leu Ile Asn Ser Phe Ala Gly Lys
```

```
                    165                 170                 175
Asn Leu Thr Ala Asp Glu Met Val Thr Leu Ser Gly Ala His Ser Ile
            180                 185                 190

Gly Val Ser His Cys Phe Ser Phe Leu Asn Arg Ile Tyr Asn Phe Ser
        195                 200                 205

Asn Thr Ser Gln Val Asp Pro Thr Leu Ser Ser Tyr Ala Asp Leu
    210                 215                 220

Leu Arg Thr Lys Cys Pro Ser Asn Ser Thr Arg Phe Thr Pro Ile Thr
225                 230                 235                 240

Val Ser Leu Asp Ile Ile Thr Pro Thr Val Leu Asp Asn Arg Tyr Tyr
                245                 250                 255

Thr Gly Val Gln Leu Thr Leu Gly Leu Leu Thr Ser Asp Gln Ala Leu
            260                 265                 270

Val Thr Glu Ala Asn Leu Ser Ala Ala Val Lys Asn Asn Ala Asp Asn
        275                 280                 285

Leu Thr Ala Trp Val Ala Lys Phe Ala Gln Ala Ile Val Lys Met Gly
    290                 295                 300

Gln Ile Gln Val Leu Thr Gly Thr Gln Gly Glu Ile Arg Thr Asn Cys
305                 310                 315                 320

Ser Val Val Asn Ser Ala Ser Leu Gly Asp Ile Val Met Ala Ser Gly
                325                 330                 335

His Leu Thr Glu Val Ala Thr Ser
            340

<210> SEQ ID NO 8
<211> LENGTH: 280
<212> TYPE: PRT
<213> ORGANISM: Phoenix dactylifera

<400> SEQUENCE: 8

Met His Leu Gln Gly Cys Asp Ala Ser Val Leu Leu Asn Ser Thr Ala
1               5                   10                  15

Asn Asn Thr Ala Glu Arg Asp Ala Ala Pro Asn Asn Pro Ser Leu Arg
            20                  25                  30

Gly Phe Glu Val Ile Asp Ala Ala Lys Ser Ala Val Glu Ala Ala Cys
        35                  40                  45

Pro Gln Thr Val Ser Cys Ala Asp Ile Leu Ala Phe Ala Ala Arg Asp
    50                  55                  60

Ser Ala Asn Leu Thr Gly Asn Ile Thr Tyr Gln Val Pro Ser Gly Arg
65                  70                  75                  80

Arg Asp Gly Thr Val Ser Leu Ala Ser Glu Ala Leu Ala Asn Ile Pro
                85                  90                  95

Ala Pro Thr Phe Asn Ala Thr Gln Leu Ile Asn Ser Phe Ala Asn Lys
            100                 105                 110

Ser Leu Thr Ala Asp Glu Met Val Thr Leu Ser Gly Ala His Ser Ile
        115                 120                 125

Gly Ile Ser His Cys Ala Ser Phe Leu Asn Arg Ile Tyr Asn Phe Ser
    130                 135                 140

Asn Thr Ser Asp Val Asp Pro Thr Leu Ser Ser Ala Tyr Ala Asp Leu
145                 150                 155                 160

Leu Lys Ala Lys Cys Pro Ala Asn Ser Thr Arg Phe Thr Pro Ile Thr
                165                 170                 175

Ala Ser Leu Asp Ile Ile Thr Pro Ala Val Leu Asp Asn Met Tyr Tyr
            180                 185                 190
```

```
Thr Gly Val Gln Leu Thr Leu Gly Leu Leu Thr Ser Asp Gln Ala Leu
            195                 200                 205

Val Thr Gln Ala Asn Leu Ser Ala Ala Val Asn Asn Asn Ala Asn Asn
            210                 215                 220

Leu Thr Ala Trp Ala Ser Lys Phe Ala Leu Ala Met Val Lys Met Gly
225                 230                 235                 240

Gln Ile Gln Val Leu Thr Gly Thr Gln Gly Glu Ile Arg Thr Asn Cys
            245                 250                 255

Ser Val Val Asn Ser Gly Gly Leu Gly Tyr Val Gly Met Gly Ser Gly
            260                 265                 270

His Pro Ser Glu Val Ala Thr Ser
            275                 280

<210> SEQ ID NO 9
<211> LENGTH: 356
<212> TYPE: PRT
<213> ORGANISM: Phalaenopsis equestris

<400> SEQUENCE: 9

Met Leu Ser Leu Met Lys Gln Ile Leu Phe Leu Phe Leu Leu Ala Val
1               5                   10                  15

Ala Val Ala Pro Pro Ala Val Asn Gly Gln Leu Lys Ile Gly Phe
            20                  25                  30

Tyr Asn Gln Thr Cys Pro Ser Ala Glu Ser Val Gln Lys Thr Val
            35                  40                  45

Ala Ala Ala Ser Ala Asn Asn Thr Gly Ile Leu Ala Gly Leu Ile Arg
        50                  55                  60

Leu Phe Phe His Asp Cys Phe Val Arg Gly Cys Asp Ser Ser Val Leu
65                  70                  75                  80

Leu Asp Ser Thr Ala Asn Asn Thr Ala Glu Lys Asp Ala Pro Pro Asn
                85                  90                  95

His Pro Ser Leu Arg Gly Phe Glu Val Ile Asp Ala Ala Lys Ser Ala
            100                 105                 110

Val Glu Ala Ile Cys Pro Asn Thr Val Ser Pro Thr Thr Ala Pro Cys
            115                 120                 125

Ala Asp Ile Val Ala Phe Ala Ala Arg Asp Ala Ala Ala Leu Ser Gly
        130                 135                 140

Asn Ile Ser Tyr Gln Ile Pro Ser Gly Arg Arg Asp Gly Asn Ile Ser
145                 150                 155                 160

Leu Ala Ser Asp Ala Asn Ala Asn Leu Pro Ser Pro Leu Ser Asn Ala
                165                 170                 175

Ser Thr Leu Ile Thr Ala Phe Ala Ala Lys Asn Leu Thr Ala Asp Glu
            180                 185                 190

Leu Val Thr Leu Ser Gly Ala His Ser Ile Gly Val Ser His Cys Ser
            195                 200                 205

Ser Phe Arg Asn Arg Leu Tyr Asn Phe Ser Ser Ser Gln Gly Asp
            210                 215                 220

Pro Thr Leu Asn Pro Ala Tyr Ala Ala Leu Leu Arg Phe Ala Cys Pro
225                 230                 235                 240

Phe Asn Ser Thr Ser Gly Asn Thr Thr Val Ala Met Asp Val Leu
                245                 250                 255

Thr Pro Val Val Leu Asp Asn Phe Tyr Tyr Ile Gly Leu Lys Met Ser
            260                 265                 270

Leu Gly Leu Phe Thr Ser Asp His Ala Leu Leu Thr Gln Gly Asn Leu
            275                 280                 285
```

```
Ser Ala Ala Val Asp Asp Asn Ala Trp Asn Pro Ala Gly Trp Ala Ala
        290                 295                 300

Lys Phe Ala Arg Ala Met Val Lys Met Gly Ser Ile Gln Val Lys Thr
305                 310                 315                 320

Gly Thr Gln Gly Glu Ile Arg Arg Asn Cys Arg Val Val Asn Gly Arg
                325                 330                 335

Ser Leu Ala Asn Val Gly Pro Ala Ala Glu Glu Gln Gly Ser Ser Leu
            340                 345                 350

Val Ala Asp Met
        355

<210> SEQ ID NO 10
<211> LENGTH: 306
<212> TYPE: PRT
<213> ORGANISM: Ananas comosus

<400> SEQUENCE: 10

Met Val Ser Ile Lys Tyr Cys Arg Arg Ser Leu Val Gln Val Val Lys
1               5                   10                  15

Tyr Leu Leu Gly Cys Asp Gly Ser Val Leu Ile Asp Ser Thr Ala Asn
            20                  25                  30

Asn Thr Ala Glu Lys Asp Ala Ile Pro Asn Asn Pro Ser Leu His Gly
        35                  40                  45

Phe Glu Val Ile Asp Ala Ala Lys Ser Val Val Glu Ala Gln Cys Pro
    50                  55                  60

Glu Thr Val Ser Cys Ala Asp Ile Leu Ala Phe Ala Ala Arg Asp Ser
65                  70                  75                  80

Ile Thr Leu Thr Gly Asn Val Thr Tyr Gln Val Pro Ala Gly Arg Arg
                85                  90                  95

Asp Gly Thr Val Ser Asn Ala Ser Glu Val Ile Pro Asn Ile Pro Ala
            100                 105                 110

Pro Thr Phe Asn Ser Thr Gln Leu Ile Asn Ser Phe Gln Ala Lys Asn
        115                 120                 125

Leu Thr Ala Glu Glu Met Val Ile Leu Ser Gly Ala His Thr Val Gly
130                 135                 140

Val Ser His Cys Ser Ser Phe Leu Asn Arg Ile Tyr Asn Phe Ser Asn
145                 150                 155                 160

Thr Ser Gln Val Asp Pro Thr Met Ser Pro Ala Tyr Ala Lys Leu Leu
                165                 170                 175

Gln Ala Leu Cys Pro Ser Asn Ser Thr Arg Phe Thr Pro Ile Thr Thr
            180                 185                 190

Gly Leu Asp Val Ile Ser Pro Gly Val Leu Asp Asn Lys Tyr Tyr Val
        195                 200                 205

Gly Leu Thr Asn Ser Leu Ser Leu Leu Thr Ser Asp His Ala Leu Leu
    210                 215                 220

Thr Asp Ala Asn Leu Ser Ala Ala Val Ser Arg Phe Ala Thr His Gln
225                 230                 235                 240

Ser Ala Trp Glu Ser Lys Phe Thr Lys Ala Met Val Arg Met Gly Glu
                245                 250                 255

Ile Gln Val Leu Thr Gly Thr Glu Gly Gln Ile Arg Leu Asn Cys Arg
            260                 265                 270
```

```
Val Val Asn Asn Ala Ser Thr Thr Ala Ala Ala Ala Ala Thr Gly
        275                 280                 285

Phe Gly Ser Val Val Gly Ser Ser His Tyr Thr Ala Gly Gly Val Ala
        290                 295                 300

Thr Ile
305
```

HYBRID PEROXIDASES WITH ENHANCED ACTIVITY AND STABILITY

CROSS-REFERENCE TO RELATED APPLICATIONS

This application claims priority benefit of U.S. Provisional Application No. 62/596,728, filed Dec. 8, 2017, which application is herein incorporated by reference in its entirety.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in this invention.

REFERENCE TO A "SEQUENCE LISTING" SUBMITTED AS AN ASCII TEXT FILE VIA EFS-WEB

This application contains a Sequence Listing file named 077429-1117646-015710US_SL.txt, created on Apr. 5, 2019 and containing 25,560 bytes, which has been filed electronically in ASCII format. The material contained in this text file is hereby incorporated by reference in its entirety.

BACKGROUND OF THE INVENTION

Heme peroxidases comprise a large, structurally and catalytically diverse enzyme superfamily with representative members found throughout all kingdoms of life. These enzymes play important roles in many cellular processes, including stress-induced responses, defense mechanisms, and biosynthesis and degradation of various biological compounds. Heme peroxidases utilize peroxide to catalyze the one-electron oxidation of their respective substrates, and their catalytic mechanism is driven by the oxidation-reduction cycle of the heme-iron center. Despite conservation in general mechanism, the enzymes differ in the strength of their reduction potential, and correspondingly, in the degree of oxidative recalcitrance of the substrates that they can target. Some of the most catalytically powerful peroxidases, in terms of reduction potential, are produced and secreted by white rot basidiomycetes fungi to aid in the oxidative degradation of lignin (Hammel & Cullen, *Curr Opin Plant Biol* 11:349-355, 2008). Lignin is particularly difficult to oxidize owing to the complexity of its aromatic constituents and the diversity of linkages found throughout its structure, thus to oxidize lignin, peroxidases must generate a strong reduction potential. These high-reduction potential heme peroxidases are attractive candidates to meet the present and future needs of bio-based industry because their catalytic strength translates into an expanded substrate range, allowing them to oxidize general peroxidase targets, such as phenolic and aromatic amines, as well as more challenging substrates, such as lignin polymer models and non-phenolic aromatics (Watanabe et al., *Struct Biol* 169:226-242, 2010; Hammel & Cullen, supra).

Of the high reduction potential peroxidases, versatile peroxidase (VP), is of particular industrial interest because it has the catalytic versatility to directly oxidize a range of low- and high-reduction potential aromatic substrates and indirectly oxidize these substrates by oxidizing manganese, which acts as a diffusible oxidizer (Camarero, et al., *J Biol Chem* 274:10324-10330, 1999; Knop et al., *Appl Environ Microbiol* 82:4070-4080, 2016; Perez-Boada, et al., *J. Mol. Biol* 354:385-402, 2005). Among the heme peroxidase superfamily, VP is evolutionarily related to secretory plant and extracellular fungal heme peroxidases, and consequently, VP shares significant structural homology with these enzymes (Zamocky, et al., *Arch Biochem Biophys* 574:108-119, 2015). These peroxidases are predominantly α-helical in structure with two calcium coordination sites and numerous disulfide bridges to aid in structure stabilization (Watanabe, et al., supra; Ruiz-Duenas, et al., *J Exp Bot* 60:441-452, 2009). Key to their catalytic function, these enzymes also contain an internally coordinated heme molecule and oxidation pathways that lead from the enzyme surface to the heme center, facilitating heme access and in some cases, long-range electron transfer (LRET) (Ruiz-Duenas et al., supra; Smith & Veitch, *Curr Opin Chem Biol* 2:269-278, 1998. VP owes its catalytic versatility to the presence of three different oxidation pathways: (1) a manganese oxidation site; (2) an exposed heme edge, also found in general peroxidases that can directly oxidize phenols, amines, and small dye compounds; and (3) an LRET pathway capable of direct and indirect high-reduction potential aromatic oxidation (Knop et al., supra).

The reaction mechanism of VP can follow one of two mechanistic cycles (FIG. 1). The first of which is very similar to that of general peroxidases and enables VP to directly target low-reduction potential substrates and indirectly target high-reduction potential substrates through the oxidation of diffusible manganese (Hammel & Kullen, supra; Perez-Boada, et al., *J Mol Biol* 354:385-402, 2005). Alternatively, the addition of hydrogen peroxide can also lead to the activation of VP's LRET oxidation pathway, allowing the enzyme to directly target high-reduction potential and bulky substrates (Hammel & Cullen, Perez-Boada et al., both supra). The presence of this oxidation pathway facilitates VP's high-reduction potential and is one factor in differentiating its catalytic ability from that of general peroxidases. Another important factor in the high-reduction potential of VP is that its heme-iron is more electron-deficient than is found in general peroxidases, enabling VP to act as a stronger oxidant (Hammel & Cullen, Perez-Boada et al., both supra; Millis CD, Cai et al., *Biochemistry* 28:8484-8489, 1989). The electron-deficiency of the heme-iron is likely largely due to the residue composition of VP's heme coordination pocket and is predominantly influenced by the strength of the hydrogen bond it shares with a proximal histidine residue, resulting in a pentacoordinate ferric state (Carmarero et al., Perez-Boada et al., both supra; Banci et al., *Proc Natl Acad Sci USA* 88:6956-6960, 1991).

A major limiting factor in the industrial application of VP is that, despite its high oxidative power and substrate versatility, it functions under a fairly narrow range of in vitro conditions and has a relatively short half-life at its optimal pH (pH 3-4) (Saez-Jimenez, et al. *PLoS One* 10:e0140984, 2015). Thus, the range of VP's application and cost efficiency of its use is greatly diminished (Ayala, et al., *J Mol Microbiol Biotechnol* 15:172-180, 2008; Martinez, et al., *Curr Opin Biotechnol* 20:348-357, 2009). Heme peroxidase pH and temperature tolerance is associated with general structural stability, and a variety of structural factors have been implicated in the ability of heme peroxidases to tolerate a wide range of temperature and pH conditions. These key structural factors include: the presence of disulfide bridges and calcium coordination sites; surface charge and pI; total α-helical content and the presence of an additional α-helix in a variable loop region; and total number of proline residues and positioning of these prolines (Fernandez-Fueyo, et al *Biotechnol Biofuels* 7:2, 2014). Although VP and its structural homologs share a similar overall fold, they vary greatly in sequence identity, which translates into substantial differences in residue composition of the enzyme surface and heme coordination pocket as well as differences in precise disulfide bridge placement. Interestingly, one of the most temperature and pH tolerant heme peroxidases was identified from the leaves of the royal palm tree *Roystonea regia* (Sakharov, et al., *Plant Sci* 161:853-86, 2001). Royal palm tree peroxidase (RPTP) is a member of the plant heme peroxidase superfamily and structural homolog of VP, but it displays thermal stability on par with that of thermophilic microbial enzymes over a broad pH range (pH 2.8-10.3) (Watanabe et al. supra; Zamorano, et al., *Biochimie* 90:1737-1749, 2008).

Structural stability and its effect on temperature and pH tolerance is likely due to a combination of factors, rather than a single factor alone, and thus engineering efforts to enhance the temperature and pH tolerance of VP to improve the feasibility of its industrial use requires consideration of many different structural aspects. There have been several engineering endeavors directed at improving the pH stability of VP through directed evolution (Saez-Jimenez, et al., *Biochem J* 473:1917-1928, 2016) and rational design through mutagenesis of surface exposed residues (Saez-Jimenez, et al., supra; Fernandez-Fueyo, et al., *Biotechnol Biofuels* 7:114, 2014). These engineering methods predominantly sought to leave VP's catalytic components untouched, and thus, focused on residue substitutions far from the oxidation pathways. In contrast to these previous methods, we describe a structure-guided approach to the rational design of a peroxidase with the high-reduction potential and substrate range of a VP but with enhanced temperature and pH tolerance of RPTP. To achieve this, we drew on the wealth of biochemical and structural information available on VP and RPTP, utilizing RPTP as a structural scaffold into which we built the catalytic components (oxidation pathways and heme coordination pocket architecture) of VP. This engineered peroxidase, VP2.0, combines the unique properties of these two enzymes—the catalytic versatility to oxidize manganese and low- and high-reduction potential substrates and an enhanced temperature and pH tolerance to outperform its catalytic parent over time.

BRIEF SUMMARY OF THE INVENTION

In contrast to previous methods, we describe a structure-guided approach to the design of a peroxidase with the high-reduction potential and substrate range of a VP but with enhanced temperature and pH tolerance of RPTP. Provided herein are peroxidases with the high-reduction potential and substrate range of a VP, but with enhanced temperature and pH tolerance of RPTP.

DETAILED DESCRIPTION OF THE INVENTION

Introduction

Figure 1:
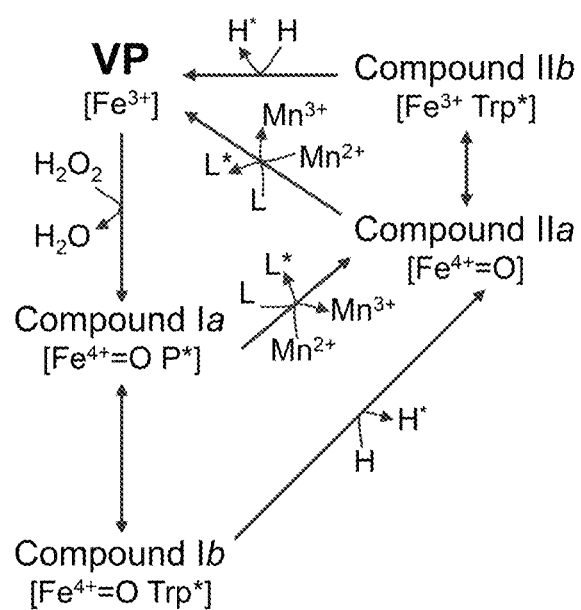
FIG. 1 Catalytic cycle of versatile peroxidases. The catalytic cycle for versatile peroxidases (VP) proposed by Perez-Boada, et al. involves formation of Compound Ia/Ib upon a two-electron oxidation of the heme-iron center by hydrogen peroxide. The resting iron (III) state is oxidized to form the iron (IV)-oxo and heme porphyrin cation radical (P*) (Compound Ia) or or the iron (IV)-oxo and tryptophan radical (Compound Ib). Formation of Compound Ia represents VP's low-reduction potential oxidation route: From Compound Ia, the enzyme can then oxidize manganese or low reduction potential aromatic substrates (L) via its manganese oxidation site or exposed heme edge, respectively, to yield Compound IIa (iron (IV)-oxo) and oxidize a second manganese or low reduction potential substrate to return to its resting state. Alternatively, once Compound Ib is formed, VP can target high-reduction potential substrates (H) through its LRET pathway to form either Compound IIa/IIb. From Compound IIa, manganese or a low reduction potential substrate can be oxidized, or from Compound IIb (iron (III)-Trp radical), an additional high-reduction potential substrate can be oxidized to return VP to its resting state.

Described herein are hybrid peroxidase proteins that oxidize manganese and are active on high-reduction potential substrates, but are active over a wide range of temperatures, e.g., from about 10° C. to about 75° C.; and under acidic conditions, e.g., pH ranging from about 2.0 up to about 7.0. The hybrid peroxidases incorporate the catalytic function of a versatile peroxidase with respect to activity on manganese substrates and high-reduction potential substrates with the stability of peroxidases from plants, such as royal palm.

Definitions

As used herein, the singular forms "a," "an," and "the" include plural referents unless the content clearly dictates otherwise. Thus, for example, reference to "a polypeptide" may include two or more such molecules, and the like.

As used herein, the terms "about" and "approximately," when used to modify an amount specified in a numeric value or range, indicate that the numeric value as well as reasonable deviations from the value known to the skilled person in the art, for example ±20%, ±10%, or ±5%, are within the intended meaning of the recited value.

The terms "wild-type," "native," and "naturally occurring" as used herein with respect to a polypeptide refers to the polypeptide sequence as it occurs in nature.

In the context of this invention, the term "mutant" with respect to a mutant polypeptide or mutant polynucleotide is used interchangeably with "variant". A variant with respect to a given wildtype heme peroxidase reference sequence can include naturally occurring allelic variants. A "non-naturally" occurring heme peroxidase refers to a variant or mutant heme peroxidase polypeptide that is not present in a cell in nature and that is produced by genetic modification, e.g., using genetic engineering technology or mutagenesis techniques, of a native heme peroxidase polynucleotide or polypeptide. A "variant" includes any heme peroxidase comprising at least one amino acid mutation with respect to wild type. Mutations may include substitutions, insertions, and deletions.

A polynucleotide or polypeptide is "heterologous" to an organism or a second polynucleotide or polypeptide sequence if it originates from a foreign species, or, if from the same species, is modified from its original form. For example, a "heterologous" sequence includes a native heme peroxidase having one or more mutations relative to the native heme peroxidase amino acid sequence.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified polypeptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acid is also meant to include—amino acids having L or D configuration at the α-carbon.

A "non-natural amino acid" is included in the definition of an amino acid and refers to an amino acid that is not one of the 20 common naturally occurring amino acids or the rare naturally occurring amino acids e.g., selenocysteine or pyrrolysine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Amino acid polymers may comprise entirely L-amino acids, entirely D-amino acids, or a mixture of L and D amino acids.

Heme peroxidase polypeptide sequences that are substantially identical to a reference sequence include "conservatively modified variants." One of skill will recognize that individual changes in a nucleic acid sequence that alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged or polar amino acids can be sub-divided into sub-groups including: a "positively-charged sub-group" comprising Lys, Arg and His; a "negatively-charged sub-group" comprising Glu and Asp; and a "polar sub-group" comprising Asn and Gln. In another example, the aromatic or cyclic group can be sub-divided into sub-groups including: a "nitrogen ring sub-group" comprising Pro, His and Trp; and a "phenyl sub-group" comprising Phe and Tyr. In another further example, the aliphatic group can be sub-divided into sub-groups, e.g., an "aliphatic non-polar sub-group" comprising Val, Leu, Gly, and Ala; and an "aliphatic slightly-polar sub-group" comprising Met, Ser, Thr and Cys. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —$NH_2$ can be maintained. In some embodiments, hydrophobic amino acids are substituted for naturally occurring hydrophobic amino acid, e.g., in the active site, to preserve hydrophobicity.

The terms "identical" or percent "identity," in the context of two or more polypeptide sequences (or two or more nucleic acids), refer to two or more sequences or subsequences that are the same or have a specified percentage of amino acid residues or nucleotides that are the same, e.g., at least 50% identity, preferably at least 55% or 60% identity, or at least 65%, 70%, 75%, 80%, 85%, 90%, 91%, 92%, 93%, 94%, 95%, 96%, 97%, 98%, 99% or 100% identity, over a specified region when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters are used. Alternatively, sequences may be aligned by hand to determine the percent identity.

The terms "corresponding to", "determined with reference to", or "numbered with reference to" when used in the context of the identification of a given amino acid residue in a polypeptide sequence based on comparison to another polypeptide sequence, refers to the position of the residue of a specified reference sequence when the given amino acid sequence is maximally aligned and compared to the reference sequence. Thus, for example, a residue in a polypeptide "corresponds to" an amino acid at a position in SEQ ID NO:1 when the residue aligns with the amino acid in SEQ ID NO:1 when optimally aligned to SEQ ID NO:1. The polypeptide that is aligned to the reference sequence need not be the same length as the reference sequence and may or may not contain a starting methionine.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide is introduced into a host cell and is targeted to a position in the genome of the host cell such that expression of the polynucleotide sequence is driven by a promoter that is present in the host cell.

The term "host cell" as used in the context of this invention refers to a microorganism and includes an individual cell or cell culture that can be or has been a recipient of any recombinant vector(s) or isolated polynucleotide(s) of as described herein. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2017).

Heme Proxidase Modifications

Class II heme peroxidases typically refer to heme peroxidases that have the capability of oxidizing high reduction potential substrates and manganese, whereas Class III peroxidases are represented by secretory plant peroxidases related to horseradish peroxidase.

Figure 11:
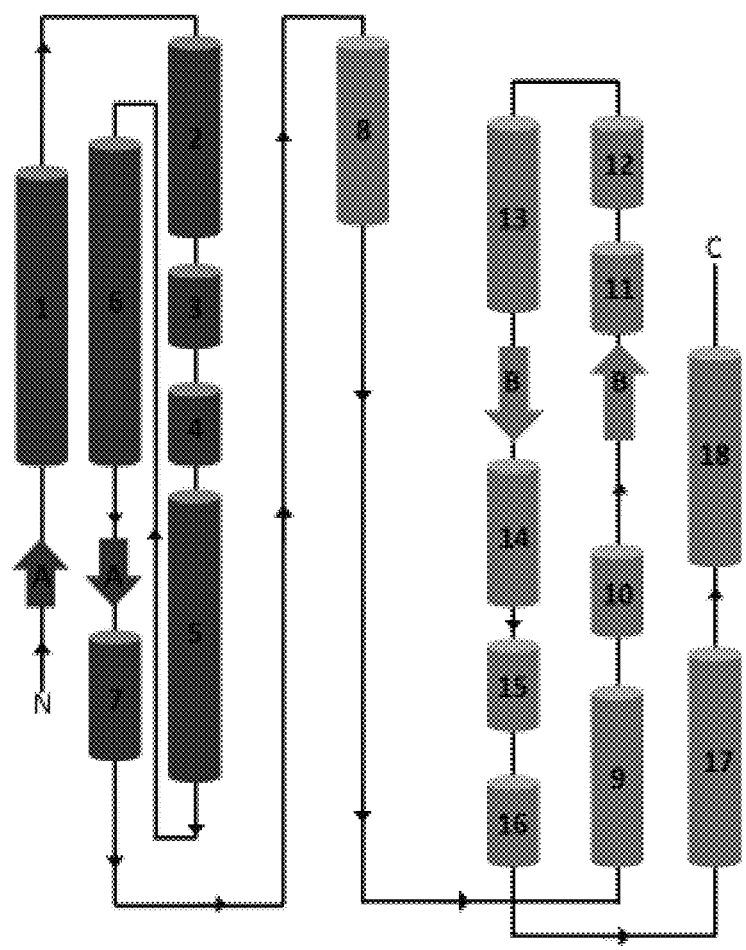
FIG. 11. Schematic of peroxidase structure. N-terminal domains are shown on the left side of the figure (structures labeled 1 to 7) and the C-terminals are shown on the right side of the figure (structural regions labeled 8 to 19). The N-terminus (first amino acid residue of the protein) is labeled with an 'N', and the C-terminus (the final amino acid residue in the protein) is labeled with a 'C'. Alpha-helices are cylinders and beta-strands are arrows. This figure was initially created by PDBsum.

Heme peroxidases are globular proteins that are 200-350 amino acid residues in length. The secondary structure of these enzymes is largely α-helical, consisting of 13-18 α-helices arranged into two domains, an N-terminal domain (FIG. 11, Helices 1-7) and a C-terminal domain (FIG. 11, Helices 8-18). The N-terminal domain contains two disulfide bridges: Bridge 1 connects Helix 1 with Helix 5, Bridge 2 connects Helix 2 and Helix 3. The N-terminal domain also contains one calcium coordination site that sits 13.5 Å from the heme-iron center. Similarly, the C-terminal domain contains two disulfide bridges: Bridge 3 connects H6 with the extreme C-terminus and Bridge 4 connects Helix 11 with Helix 13. A second calcium coordination site is located in the C-terminal domain and places the calcium ion 15.6 Å from the heme-iron center. The heme coordination pocket is formed at the interface of the N- and C-terminal domains from Helices 7, 8, 9, 10, 15, and 18, which together create a central, internal cavity with dimensions 8 Å H×26 Å W×22.5 Å D for heme coordination. This cavity is lined by hydrophobic residues and utilizes a histidine residue for pentacoordination of the heme-iron center.

Hybrid peroxidases will contain one or more openings or pathways that lead from the heme molecule to the enzyme surface. Functional and auxillary mutations can be introduced at these pathway sites in order to introduce the high-reduction potential peroxidase activity described here. The first of these pathways is commonly referred to as the 'heme edge'. The heme edge is an opening on the surface of the enzyme and it is a relatively short pathway (11 Å from the enzyme surface to the heme-iron center), allowing for closer proximity of the solvent with the heme molecule. This site is formed by Helix 3, Helix 12, and the connecting loop sequence linking Helix 7 and 8.

The second pathway of interest is located 180° away from the heme edge on the opposite face of the enzyme. The structure of this site is composed of Helices 2, 9, 17, and 18. This site is the location of the long-range electron transfer (LRET) pathway that was introduced into RPTP. An important functional residue of this site is the T164W and this residue is located on the surface of the enzyme, 17.3 Å from the heme-iron center.

The third pathway is positioned 5-7 Å from the nearest propionate group of the heme molecule and 12.2 Å from the heme-iron center. This site is formed by Helix 2 and the loop structure that connects Helices 1 and 2, and a two-stranded, anti-parallel β-sheet (denoted β-sheet B).

Modifications to Class III peroxidases include substitutions to alter enzymatic activity to oxidize manganese and high reduction potential substrates. In some embodiments, amino acids substitutions are introduced into a polypeptide sequence that has at least 70% identity, or at least 75% identity, at least 80% identity, at least 85% identity, at least 90% identity, or at least 95% identity to SEQ ID NO:1. In some embodiments, a heme peroxidase that is modified comprises the amino acid sequence of SEQ ID NO:5, 6, 7, 8, 9, or 10; or has at least 90%, or at least 95%, identity to the amino acid sequence of SEQ ID NO:5, 6, 7, 8, 9, or 10. In some embodiments, a modified heme peroxidase in accordance with the invention comprises at least one, typically at least two or at least three amino acid substitutions, at positions corresponding to positions 152, 222, 270, 140, 142, 143, 260, 164, 274, 264, 278, 31, 35, 173, 29, and 75 as determined with reference to SEQ ID NO:1. In some embodiments, a modified heme peroxidase in accordance with the invention comprises at least four, or at least five, or at least six substitutions, at positions corresponding to positions 152, 222, 270, 140, 142, 143, 260, 164, 274, 264, 278, 31, 35, 173, 29, and 75 as determined with reference to SEQ ID NO:1. In some embodiments, a modified heme peroxidase of the invention comprises at least seven, eight, nine, or ten substitutions, at positions corresponding to positions 152, 222, 270, 140, 142, 143, 260, 164, 274, 264, 278, 31, 35, 173, 29, and 75 as determined with reference to SEQ ID NO:1. In some embodiments, a modified heme peroxidase comprises at least eleven, twelve, or thirteen substitutions, at positions corresponding to positions 152, 222, 270, 140, 142, 143, 260, 164, 274, 264, 278, 31, 35, 173, 29, and 75 as determined with reference to SEQ ID NO:1. In some embodiments, a modified heme peroxidase comprises at least fourteen, fifteen, or sixteen substitutions at positions corresponding to positions 152, 222, 270, 140, 142, 143, 260, 164, 274, 264, 278, 31, 35, 173, 29, and 75 as determined with reference to SEQ ID NO:1.

In some embodiments, a modified peroxidase of the present invention comprises an aromatic substitution, relative to a native heme peroxidase sequence such as SEQ ID NO:1, at position 222, 142, and/or 164. In some embodiments, a modified peroxidase of the present invention comprises a non-polar amino acid substitution, relative to a native heme peroxidase sequence such as SEQ ID NO:1, at position 152, 264, 29, and/or 75. In some embodiments, a modified peroxidase of the present invention comprises a basic amino acid substitution, relative to a native heme peroxidase sequence such as SEQ ID NO:1, at position 270 and/or 274. In some embodiments, a modified peroxidase of the present invention comprises an acidic amino acid substitution, relative to a native heme peroxidase sequence such as SEQ ID NO:1, at position 140, 143, 260, 31, 35, and/or 173.

In some embodiments, the hybrid peroxidase comprises at least one amino acid selected from 152M, 222F, 270K, 140E, 142F, 143D, 260E, 164W, 274R, 264M, 278T, 31E, 35E, 173D, 29A, and 75A. In some embodiments, a W is substituted for a naturally occurring amino acid at position 164 as determined with reference to SEQ ID NO:1. In typical embodiments, a hybrid peroxidase of the invention comprises a W at position 164 and an acidic residue, e.g., D or E, at position 260, wherein one or both of these positions are substituted relative to a native heme peroxidase sequence, e.g., SEQ ID NO:1.

In some embodiments, the hybrid peroxidase comprises amino acid substitutions at positions T164 and A260 (in the LRET pathway); and G31, G35, and R75 to provide the ability to coordinate one manganese atom, which positions are determined with reference to SEQ ID NO:1. In some embodiments, the substitutions comprise at least one, or at least two, three, or four substitutions selected from T164W, A260E, G31E, G35E, and R75A. In some embodiments, the hybrid peroxidase comprises substitutions T164W, A260E, G31E, G35E, and R75A. In some embodiments, the hybrid peroxidase additionally comprises a substitution at at least one of the following eight positions: position V173 (involved in coordinating manganese), at positions F152, L222, and A270 (involved in heme coordination), S140, L142, and F143 at the heme edge, and N264 in the LRET. In some embodiments, two, three, four, five, six, seven, or all eight positions are substituted. In some embodiments, the substitutions at one, two three, four, five, six, seven, or all eight positions are selected from the following: V173D, F152M, L222F, A270K, S140E, L142F, F143D, and N264M. In some embodiments, the hybrid peroxidase further comprises a mutation at K274, A278, or N29 as determined with referenced to SEQ ID NO:1. In some embodiments, the mutation is K274R, A278T, or N29A.

In some embodiments, a modified heme peroxidase of the invention, e.g., as described in the preceding paragraphs, has at least 70%, at least 75%, at least 80%, at least 85%, at least 90%, or at least 95% identity to SEQ ID NO:3.

Class III peroxidases that can be modified in accordance with the invention to use manganese and high reduction potential substrates include peroxidases that have substantial three-dimensional structural similarly to the three-dimensional structure of the Royal Palm heme peroxidase sequence SEQ ID NO:1 (DB ID: 3HDL). "Substantial" three-dimensional structural similarity as used herein includes proteins that have an RMSD score of less than 2.0 Angstroms and a DALI Z-score of about 25 or greater compared to PDB:3HDL.

Structural models for evaluation of structural similarity can be generated using any number of modeling programs, e.g., using RosettaCM, SWISS-MODEL, MODELLER, 3D-JIGSAW, ModPipe, Fugue, HHPred, i-Tasser, IntFOLD, M4T, ModWeb, Phyre2, RaptorX, Robetta, HHsuite, and the like. Structural models so generated can be scored for three dimensional structural similarity to the structure of the comparator sequence, i.e., in this case, the three-dimensional structure of the Royal Palm Tree heme peroxidase sequence of SEQ ID NO:1 (PDB: 3HDL). For example, a structural alignment program or methods as described herein, including one or more of TM align, the DALI server (e.g., DaliLite v. 3 available at ekhidna.biocenter.helsinki.fi/dali_server), or the cealign algorithm implemented in PyMOL (e.g., version 1.7.6 available at www.pymol.org) can be used to assess structural similarity by calculating a TM align score, Z-score, or an RMSD value respectively.

In some embodiments, an RMSD value as calculated by, e.g., cealign or other similar methods or programs, can be utilized to assess structural similarity. In some embodiments, RMSD cutoffs calculated as described herein of less than about 3 Å, 2.5 Å, 2 Å, or 1.6 Å can be used as a cutoff for structural similarity.

In some embodiments, a Z-score calculated by the DALI server is used to assess structural similarity. For example, a Z-score cut-off of at least about 20 or greater can be used to identify structurally related sequences. In some embodiments a Z-score of at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, or 62 can be used to identify a Class III heme peroxidase sequence that is modified as described herein to be capable of oxidizing manganese and high-reduction potential substrates.

In some embodiments, heme peroxidases structurally similar to heme peroxidase structure PDB ID: 3HDL comprise one or more aromatic amino acids at positions in the structure corresponding to positions 222, 142, and 164 of 3HDL. In some embodiments, a modified peroxidase of the present invention comprises one or more non-polar amino acids at positions in the structure corresponding to 152, 264, 29, and 75 of 3HDL. In some embodiments, a modified peroxidase of the present invention comprises one or more basic amino acids at positions corresponding to positions 270 and 274 of 3HDL. In some embodiments, a modified peroxidase of the present invention comprises one or more acidic amino acids at positions corresponding to positions 140, 143, 260, 31, 35, and 173 of 3HDL. In some embodiments, the heme peroxidase that is modified to oxidize manganese and high reduction potential substrates is a heme peroxidase of a PDB ID structure: 4USC, 4A5Q, 1SCH, 4CUO, 1GWU, 1PA2, 2YLJ, 1W4W, 1H5C, 1H5F, 1GO4, 6ATJ, 1KZM, 2ATJ, 3ATJ, 1GX2, 5TWT, 4ATJ, 1GGJ, 1FHF, 5AOG, 1BGP, 5JPR, 2WD4, 2GHH, 2GHC, 1V0H, 2VNZ, 2CL4, 2GHE, 2X16, 2VCS, 3ZCQ, 1OAG, 2XJ6, 2Y6A, 1IYN, LOAF, 2VCF, 2XIF, or 1APX.

In some embodiments, the hybrid peroxidase comprises amino acid substitutions in a structure that aligns with an RMSD of 2.5 A or less to 3HDL. In some embodiments, the hybrid peroxidases comprises substitutions at positions corresponding to positions T164 and A260 (the LRET pathway); and G31, G35, and R75 (to coordinate manganese) of 3HDL. In some embodiments, the substitutions comprise at least one, or at least two, three, or four substitutions selected from T164W, A260E, G31, G35E, and R75A. In some embodiments, the hybrid peroxidase comprises substitutions T164W, A260E, G31, G35E, and R75A. In some embodiments, the hybrid peroxidase additionally comprises a substitution at at least one of the following eight positions corresponding to the following positions of 3HDL: position V173 (involved in coordinating manganese), at positions F152, L222, and A270 (involved in heme coordination), S140, L142, and F143 at the heme edge, and N264 in the LRET. In some embodiments, two, three, four, five, six, seven, or all eight positions are substituted. In some embodiments, the substitutions at one, two three, four, five, six, seven, or all eight positions are selected from the following: V173D, F152M, L222F, A270K, S140E, L142F, F143D, and N264M. In some embodiments, the hybrid peroxidase further comprises a mutation at a positions corresponding to K274, A278, or N29 of 3HDL. In some embodiments, the substitution is K274R, A278T, or N29A.

Hybrid Peroxidase Expression

To use isolated sequences in the above techniques, recombinant DNA vectors suitable for transformation of host cells are prepared. Preparation of recombinant vectors is well known in the art. In some embodiments, an expression vector that comprises an expression cassette that comprises the gene further comprises a promoter operably linked to the gene. In some embodiments, a promoter and/or other regulatory elements that direct transcription of the gene are endogenous to the microorganism and an expression cassette comprising the gene encoding the hybrid peroxidase is introduced, e.g., by homologous recombination, such that the heterologous gene is operably linked to an endogenous promoter and is expression driven by the endogenous promoter.

Expression of the gene encoding a hybrid peroxidase can be controlled by a number of regulatory sequences including promoters, which may be either constitutive or inducible; and, optionally, repressor sequences. Examples of suitable promoters for directing the transcription of the nucleic acid constructs of the present invention in a bacterial host cell, are the promoters obtained from the *E. coli* lac operon, *Streptomyces coelicolor* agarase gene (dagA), *Bacillus subtilis levansucrase* gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase genes (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25) and tryptophan promoter; and bacteriophage promoters, such as a T7, M13, or λ phage promoter. Further promoters are described in "Useful proteins from recombinant bacteria" in Scientific American, 1980, 242: 74-94; and in Sambrook & Russell, supra.

In some embodiments, a hybrid peroxidase may be expressed in a fungal host cell. Examples of suitable promoters for directing the transcription of the nucleic acid constructs of the present invention in a filamentous fungal host cell include, but are not limited to, promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as mutant, truncated, and hybrid promoters thereof.

Suitable promoters of use in a yeast host cell include promoters obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

Alternatively, a hybrid peroxidase of the invention may be produced in other expression systems, including insect, plant or mammalian expression systems. Such systems are well known in the art.

An expression vector may also comprise additional sequences that influence expression of a gene encoding a hybrid peroxidase. Such sequences include enhancer sequences or other sequences such as transcription termination sequences, and the like.

A vector expressing a nucleic acid encoding a hybrid peroxidase may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated.

An expression vector of the invention preferably contains one or more selectable markers which permit easy selection of transformed hosts. For example, an expression vector my comprise a gene that confers antibiotic resistance (e.g., ampicillin, kanamycin, chloramphenicol or tetracycline resistance) to the recombinant host organism, e.g., a bacterial cell such as *E. coli*, that comprises the vector. Any suitable markers for other microbial host cells, such as yeast host and filamentous fungal host cells, may also be employed when using such a host cell expression system.

Although any suitable expression vector may be used to incorporate the desired sequences, including expression systems derived from a bacterium, a virus, a cosmid, a yeast, and a plant. Readily available bacterial expression vectors include, without limitation: plasmids, such as pSClOl, pBR322, pBBRlMCS-3, pUR, pEX, pMRlOO, pCR4, pBAD24, pUC19; bacteriophages, such as Ml 3 phage and T7 page; and λ phage. Suitable vectors can be maintained in low, medium, or high copy number in the host cell. One of ordinary skill in the art can readily determine whether any particular expression vector is suited for any given host cell.

Host Cells

Any number of host cells, e.g., microorganism host cells, can be transformed with an expression vector comprising a gene encoding a hybrid peroxidase in accordance with the invention. In some embodiments, the host cell is prokaryotic, such as bacterial host cells. Examples of bacterial host cells include, without limitation, species assigned to the *Escherichia, Enterobacter, Azotobacter, Erwinia, Bacillus, Clostridium, Enterococcus, Lactobacillus, Lactococcu, Oceanobaciilus, Pseudomonas, Klebsiella, Proteus, Salmonella, Serratia, Shigella, Staphococcus, Strpeotcoccus, Streptomyces, Rhizobia, Vitreoscilla, Synechococcus, Synechocystis,* and *Paracoccus* taxonomical classes. In some embodiments, the prokaryotic host cells are *E. coli*, or a *Bacillus* sp. such as *Bacillus subtilis*. In some embodiments, a host cell is a cyanobacterial host cell or a microalgae host cell.

In some embodiments, the host cell is a yeast. Examples of yeast host cells include *Candida, Hansenula, Kluyveromyces, Pichia, Saccharomyces, Schizosaccharomyces,* or *Yarrowia* host cells. In some embodiments, the yeast host cell is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* cell. In some embodiments, the yeast host cell is a *Kluyveromyces lactis* cell. In another embodiment, the yeast host cell is a *Yarrowia lipolytica* cell.

In other embodiments, the host cell is a filamentous fungal cell. In some embodiments, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Malbranchea, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell. For example, a filamentous fungal host cell may be an *Aspergillus awamori, Aspergillus fumigatus, Aspergillus foetidus, Aspergillus japonicus, Aspergillus nidulans, Aspergillus niger* or *Aspergillus oryzae* cell. In other embodiments, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In further embodiments, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Malbranchea cinnamomea, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell. In some embodiments, the filamentous fungal host cell is *Ustilago maydis*.

In additional embodiments, the host cell may be a plant cell, insect cell, mammalian cell, avian cell, or other host cell.

The host cells of the present invention may be genetically modified in that recombinant nucleic acids have been introduced into the host cells, and as such the genetically modified host cells do not occur in nature. The suitable host cell is one capable of expressing one or more nucleic acid constructs encoding one or more proteins for different functions.

In some embodiments, the host cell naturally produces any of the proteins encoded by the polynucleotides of the invention. The genes encoding the desired proteins may be heterologous to the host cell or these genes may be endogenous to the host cell but are operatively linked to heterologous promoters and/or control regions which result in the higher expression of the gene(s) in the host cell. In other embodiments, the host cell does not naturally produce the desired proteins, and comprises heterologous nucleic acid constructs capable of expressing one or more genes necessary for producing those molecules.

Oxidation Activity of Hybrid Peroxidases

The hybrid peroxidases of the invention are useful biocatalysts, which can be used in mild and environmentally benign methods for industrial processes and other applications. Hybrid peroxidases according to the invention can be used for the remediation of pollutants such as pesticides, pharmaceuticals, and household chemicals by oxidizing the pollutants and converting them to less harmful derivatives. For example, hybrid peroxidases can be used for the oxidation of pesticides, such as organochlorine pesticides (including, but not limited to, dicofol, dieldrin, dienochlor, endosulfan, tetradifon, and the like), organophosphorus pesticides (including, but not limited to, acephate, chlorpyrifos, chlorpyrifos-methyl, diazinon, dimethoate, disulfoton, ethion, fenitrothion, isoxathion, malathion, parathion, parathion-methyl, profenofos, quinalphos, and the like), and pyrethroids (including, but not limited to, cyphenothrin, etofenprox, permethrin, phenothrin, pyrethrum, and the like). The hybrid peroxidases can also be used for oxidation and remediation of polycyclic aromatic hydrocarbon pollutants (e.g., anthracene, phenanthrene, tetracene, chrysene, triphenylene, pentacene, pyrene, benzo[a]pyrene, corannulene, perylene, benzo[ghi]perylene, coronene, ovalene, fluorene, benzo[c]fluorene, and the like) and other aromatic substances, (e.g., benzene, phenol, naphthalene, tetralin, 2,4-dichlorophenol, pentachlorophenol, and the like).

Hybrid peroxidases according to the invention can also be used to facilitate the production of useful compounds from lignocellulosic biomass. Lignocellulosic biomass, a polymeric material containing lignin, cellulose and hemicellulose, typically constitutes about 85% mass of most plant biomass. Cellulose and hemicellulose can be depolymerized by acid- or enzyme-catalyzed hydrolysis. Lignins are typically much more recalcitrant to depolymerization, and cleavage of the principal bonds in the lignin polymer generally proceeds through oxidation. Lignin is a phenylpropane polymer of monolignol monomers. It is generally found as an integral part of the secondary cell walls of plants and certain types of algae. There are three monolignol monomers, methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Lignin generally contain small amounts of incomplete or modified monolignols, and other monomers are prominent in non-woody plants. Hybrid peroxidases of the invention can be used for the oxidative depolymerization of lignin polymers. Polymeric lignin compounds with molecular weights below 1 kDa can be particularly amenable to oxidation by certain hybrid peroxidases. The hybrid peroxidases can also be used for oxidation of other lignin-derived compounds including, but not limited to, p-coumaryl alcohol, sinapyl alcohol, coniferyl alcohol, p-coumaric acid, phenylcoumaran, pinoresinol, dibenzodioxocin, vanillin, veratryl alcohol, guaiacol, catechol, and syringaldazine.

Hybrid peroxidases according to the invention can be used for decolorization of synthetic dyes in photography, textile manufacturing, and other industrial processes. For example, hybrid peroxidases can be used for the oxidation and decolorization of dyes such as cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and boron-dipyrromethene dyes.

Examples of azo dyes include, but are not limited to, Acid orange 5, Acid orange 7, Acid Red 13, Acid red 88, Alcian yellow, Alizarine Yellow R, Allura Red AC, Amido black 10B, Aniline Yellow, Arylide yellow, Azo violet, Azorubine, Basic Red 18, Biebrich scarlet, Bismarck brown Y, Black 7984, Brilliant Black BN, Brown FK, Brown HT, Chrysoine resorcinol, Citrus Red 2, Congo red, D&C Red 33, Direct Blue 1, Direct Blue 15, Disperse Orange 1, Fast Yellow AB, Hydroxynaphthol blue, Janus Green B, Lithol Rubine BK, Metanil Yellow, Methyl orange, Methyl red, Methyl yellow, Mordant Brown 33, Mordant red 19, Oil Red O, Oil Yellow DE, Orange B, Orange G, Orange GGN, Para Red, Pigment Yellow 10, Ponceau 2R, Ponceau 3R, Ponceau 4R, Ponceau 6R, Ponceau S, Prontosil, Reactive Black 5, Reactive Blue 38, Reactive Orange 16, Reactive Red 2, Reactive Red 120, Red 2G, Scarlet GN, Solvent Red 26, Solvent Yellow 124, Sudan Black B, Sudan I, Sudan II, Sudan III, Sudan IV, Sudan Red 7B, Sudan Red G, Sudan stain, Sudan Yellow 3G, Sunset Yellow FCF, Tartrazine, Trypan blue, and Yellow 2G.

Examples of phthalocyanine dyes include, but are not limited to, Phthalocyanine green, Disodium phthalocyanine, Dilithium phthalocyanine, Phthalocyanine chloroaluminum, Cobalt(II) phthalocyanine, Copper(II) phthalocyanine ((also referred to as Pigment Blue 15), Copper(II) 2,9,16,23-tetra-tert-butylphthalocyanine, Copper(II) 2,3,9,10,16,17,23,24-octafluorophthalocyanine, Copper(II) 5,9,14,18,23,27,32, 36-octabutoxy-2,3-naphthalocyanine, Copper(II) 1,2,3,4,8, 9,10,11,15,16,17,18,22,23,24,25-hexadecafluorophthalocyanine, Iron(II) phthalocyanine, Lead(II) phthalocyanine, Manganese(II) phthalocyanines, Nickel(II) phthalocyanine, Tin(II) phthalocyanine, Tin(IV) phthalocyanine dichloride, Tin(IV) 2,3-naphthalocyanine dichloride, Titanyl phthalocyanine, and Zinc phthalocyanines. Examples of anthracene derivative dyes include, but are not limited to, Alizarin, Alizarin Red S, Alizarin-3-methyliminodiacetic acid, Alizarin Blue Black B, Reactive Blue 4, Remazol Brilliant Blue R, Disperse Orange 11, Quinalizarin, Acid Green 25, and Orange G.

The activity of a hybrid peroxidase according to the invention can be assessed by measuring the ability of the peroxidase to oxidize a substrate, e.g., an aromatic organic compound or a manganese salt, at a particular temperature and/or a particular pH. Activity can be assessed by measuring the oxidation of ABTS (i.e., 2,2'-azino-bis(3-ethylbenzothiazoline-6-sulfonic acid) diammonium salt); DMP (i.e., 2,6-dimethylphenol); vertatryl alcohol (i.e., 3,4-dimethoxybenzyl alcohol); Reactive Black 5 ("RB5," i.e., 4-amino-5-hydroxy-3,6-bis((4-((2-(sulfooxy)ethyl)sulfonyl)phenyl) azo)-2,7-naphthalenedisulfonic acid tetrasodium salt); or another aromatic organic compound. Activity can also be assessed by measuring the oxidation of manganese(II) sulfate, manganese(II) formate, manganese(II) nitrate, manganese(II) chloride, manganese(II) fluoride, manganese(II) iodide, or another manganese salt or the hydrate of a manganese salt. As a non-limiting example, RB5 oxidation can be measured by the disappearance of absorption at 598 nm upon incubation with a hybrid peroxidase in the presence of hydrogen peroxide. ABTS oxidation can be measured by absorption at 436 nm due to the formation of ABTS radical cation upon incubation with a hybrid peroxidase in the presence of hydrogen peroxide. Alternatively, oxidation of manganese(II) sulfate can be measured by absorption at 266 nm, due to the formation of manganese(III) malonate upon incubation with a hybrid peroxidase in the presence of hydrogen peroxide and sodium malonate.

A substrate such as RB5, ABTS, or manganese(II) sulfate can be incubated with the hybrid peroxidase for any length of time, typically ranging from a few minutes to a few hours or a longer. In general, the substrate is present in excess with respect to the hybrid peroxidase. For example, the concentration of the substrate in a test reaction mixture will typically range from around 100 µM to around 50 mM, while the concentration of the hybrid peroxidase in the reaction mixture will range from about 1 nM to about 100 nM. The amount of hybrid peroxidase in the reaction mixture can also be expressed in activity units, i.e., the amount of enzyme needed to produce a particular amount of product under defined conditions. In certain embodiments, a hybrid peroxidase "unit" is defined as the amount of peroxidase necessary to produce 1 nanomole of oxidized ABTS per minute at 30° C. and pH=3.

Incubation of a test substrate with a hybrid peroxidase can be conducted at temperatures ranging from around 4° C. to around 90° C. (e.g., about 25-37° C.) at acidic, neutral, or basic pH (e.g., pH 3-10). The pH can be maintained by employing a suitable buffer (e.g., 2-(N-morpholino)-ethanesulfonic acid (MES), N-cyclohexyl-2-aminoethanesulfonic acid (CHES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, citric acid, sodium citrate, sodium acetate, sodium tartrate, sodium malonate, sodium borate, and the like). Typically, buffers will be used in concentrations ranging from about 100 µM to about 100 mM (e.g., from about 10 mM to about 100 mM, or from about 25 mM to about 75 mM), and hydrogen peroxide will be used in amounts ranging from about 10 µM to about 10 mM (e.g., from about 1 mM to about 5 mM).

In some embodiments, the ability of a hybrid peroxidase to oxidize RB5 is assayed by i) incubating the hybrid peroxidase in a reaction mixture comprising RB5 and hydrogen peroxide at a temperature ranging from 10° C. to 80° C. and pH ranging from 3 to 10, and ii) monitoring the oxidation of RB5 by measuring the disappearance of absorbance at 598 nm. In some embodiments, the incubation is conducted at around 30° C. and around pH 3. In some embodiments, the concentration of RB5 is about 200 µM and the concentration of the hydrogen peroxide is around 5 mM.

In some embodiments, the ability of a hybrid peroxidase to oxidize veratryl alcohol is assayed by i) incubating the hybrid peroxidase in a reaction mixture comprising veratryl alcohol and hydrogen peroxide at a temperature ranging from 10° C. to 80° C. and pH ranging from 3 to 10, and ii) monitoring the formation of veratraldehyde by measuring absorbance at 310 nm. In some embodiments, the incubation is conducted at around 30° C. and around pH 3. In some embodiments, the concentration of veratryl alcohol is about 1 mM and the concentration of the hydrogen peroxide is around 5 mM.

In some embodiments, the ability of a hybrid peroxidase to oxidize manganese is assayed by i) incubating the hybrid peroxidase in a reaction mixture comprising manganese(II) sulfate, hydrogen peroxide, and sodium malonate at a temperature ranging from 10° C. to 80° C. and pH ranging from 3 to 10, and ii) monitoring the formation of manganese(III) malonate by measuring absorbance at 266 nm. In some embodiments, the incubation is conducted at around 30° C. and around pH 5. In some embodiments, the concentration of manganese(II) sulfate is about 10 mM, the concentration of the hydrogen peroxide is around 1 mM, and the concentration of the sodium malonate is about 20 mM.

In some embodiments, the ability of a hybrid peroxidase to oxidize ABTS is assayed by i) incubating the hybrid peroxidase in a reaction mixture comprising ABTS and hydrogen peroxide at a temperature ranging from 10° C. to 80° C. and pH ranging from 3 to 10, and ii) monitoring the formation of ABTS radical cation by measuring absorbance at 436 nm. In some embodiments, the incubation is conducted at around 30° C. and around pH 3. In some embodiments, the concentration of ABTS is about 1 mM and the concentration of the hydrogen peroxide is around 5 mM.

The ability of a hybrid peroxidase to oxidize a particular substrate can be expressed as an activity increase with respect to a native peroxidase. For example, the ability of a hybrid peroxidase to oxidize a substrate (e.g., RB5) may be 10% higher than the ability of a native peroxidase (e.g., *Pleurotus ostreatus* VP1 according to SEQ ID NO:2) to oxidize the substrate. The ability of the hybrid peroxidase to oxidize the substrate may be 20%, 30%, 40%, 50%, 60%, 70%, 80%, 90%, 100%, 150%, or 200% higher than the ability of the native peroxidase to oxidize the substrate. Advantageously, the increased activity of the hybrid peroxidases is also observed at temperatures (e.g., 40° C. and above) and pH values (e.g., pH 4 and above) outside the narrow optimum ranges of the native peroxidases, thereby expanding the utility of the hybrid peroxidases for industry and other applications.

In one aspect, the invention further provides a kit comprising a hybrid peroxidase of the present invention, e.g., a hybrid peroxidase comprising the amino acid sequence of SEQ ID NO3; or having at least 95% identity to SEQ ID NO:3. In some embodiments, the kit further comprises reagents for conducting the desired reactions, substrates for assessing activity, and the like.

In some embodiments, a hybrid peroxidase of the present invention can be covalently or non-covalently linked to a solid support. Examples of solid supports include but are not limited to supports such as polystyrene, polyacrylamide, polyethylene, polypropylene, polyethylene, glass, silica, controlled pore glass, metals and the like. The configuration of the solid support can be in the form of beads, spheres, particles, gel, a membrane, or a surface.

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

EXAMPLES

Example 1. Design of a Hybrid Peroxidase

VP is produced by a small subset of fungal genera, *Pleurotus, Bjerkandera,* and *Lepista* (Perez-Boada, supra). Of those, one of the most well studied, in terms of structural and biochemical characterization, comes from the white rot fungi *Pleurotus ostreatus* (VP1), and served as the catalytic parent for a hybrid peroxidase, referred to herein as VP2.0. VP1 is 332 residues in length and its globular structure consists of 15 α-helices and six β-strands that are arranged into three short β-sheets(Fernandez-Fueyo, 2014, supra). It served as a model for VP2.0's heme coordination pocket and oxidation pathways. As is typical of these heme peroxidases, there are also four disulfide bridges present in VP1, two above (Cys4-Cys16 and Cys35-Cys115) and two below (Cys15-Cys279 and Cys243-Cys308) the heme plane, and two calcium coordination sites, one proximal and one distal to the heme. The heme coordination pocket of VP1 is formed by six of the α-helices and one β-sheet, which together create a central, internal cavity for heme coordination. As is typical of these heme peroxidases, there are also four disulfide bridges present in VP1, two above (Cys4-Cys16 and Cys35-Cys115) and two below (Cys15-Cys279 and Cys243-Cys308) the heme plane, and two calcium coordination sites, one proximal and one distal to the heme.

VP1's heme coordination pocket is predominantly hydrophobic and contains three key functional residues. His170 is important for pentacoordination of the heme-iron, and His40 and Arg44 catalyze the heterolytic cleavage of the oxygen-oxygen bond in hydrogen peroxide to stimulate reaction progression (Rodriguez-Lopez, et al., *J Am Chem Soc* 123: 11838-11847, 2001) (FIG. 1). VP1's exposed heme edge is well-conserved among heme peroxidases (14), and in VP1, this site is composed of Pro77, Ala78, Ala80, Glu141, Pro142, Phe143, Lys177, Val 178, and Lys216. Glu141 is predicted to control the interaction of substrates with heme, either promoting or preventing interactions depending on its orientation (Morales, et al., *J Biol Chem* 287:41-53-41067, 2012). The flanking residues contribute to the size and local charge of the site, and the geometry of their configuration in VP1 is wide enough to allow single ring aromatics to interact directly with heme (Morales et al., supra). The manganese site of VP1 utilizes Glu37, Glu41, and Asp176 to coordinate manganese, and sits on the enzyme surface in close proximity to the heme-proprionate group (Fernandez-Fueyo et al., 2014, supra). Finally, VP1's LRET pathway directly involves a surface exposed tryptophan (Trp165) and a neighboring Leu166 to facilitate substrate oxidation (Fernandez-Fueyo et al., 2014, supra). Glu244 and Glu162 create an electronegative local environment around Trp165, which stabilizes the reactive cation radical state of Trp165, and Glu244 further stabilizes the radical by forming a hydrogen bond with the tryptophan indole ring nitrogen (Ruiz-Duenas, et al., supra). This region, from the enzyme surface to the heme coordination pocket, is also lined by: Val 161, Glu162, Val 164, Ser169, Met248, Arg258, and Met263.

Figure 2:
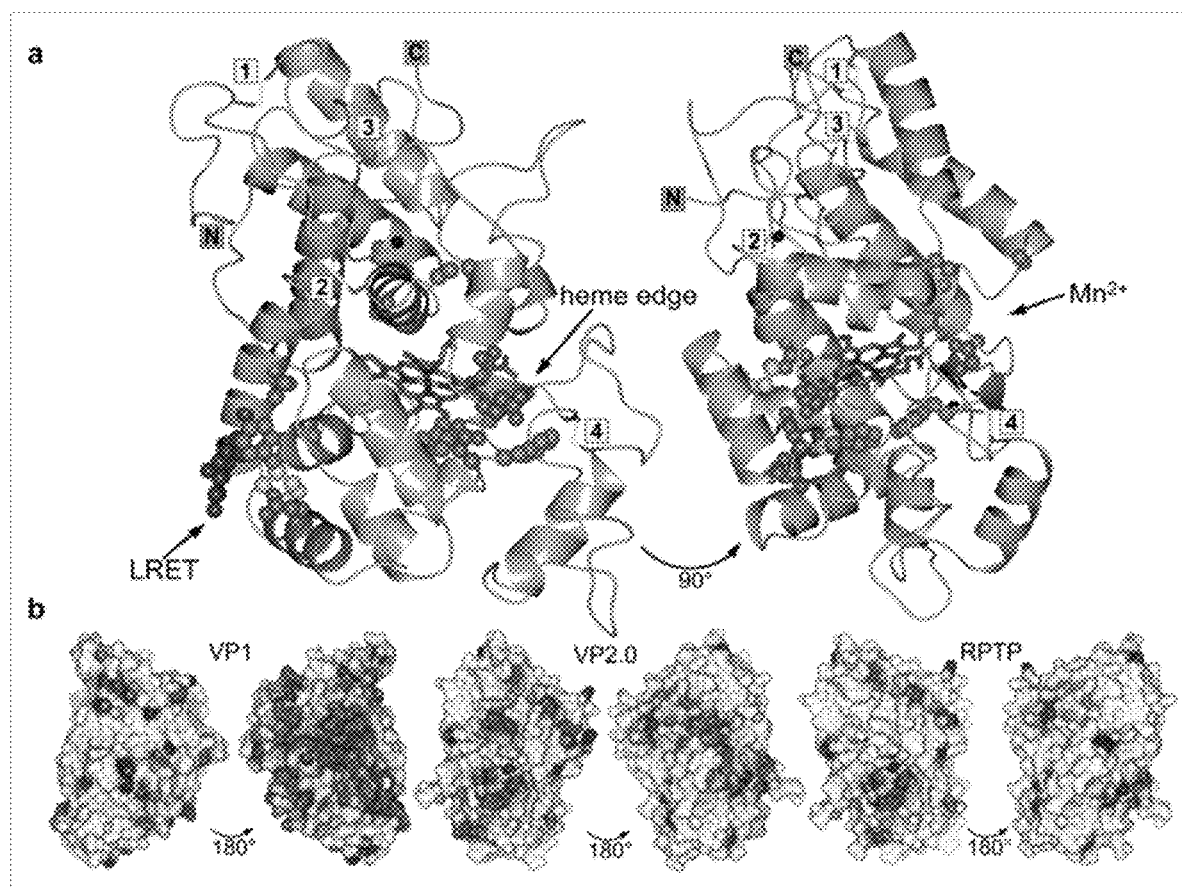
FIG. 2, Panels a-b. The predicted structure and surface properties of VP2.0. Panel a: The structure model of VP2.0 (gray) is shown coordinated with heme and two calcium ions (black). VP2.0's four disulfide bonds are displayed and numbered according to their location within the VP2.0 sequence, 1-4. The 16 point mutations required to complete its oxidation pathways and heme coordination pocket are and include aromatic residues; non-polar residues; polar residues; basic residues, acidic residues; and sulfur-containing residues. The structure model of VP2.0 was generated by Phyre2 (Kelley et al., *Nat Protoc* 10:845-858, 2015). Panel b: The electrostatic surface potentials of VP1, VP2.0, and RPTP are shown (red, negative charge; blue, positive charge). One of the most apparent differences between VP2.0 and VP1 is that VP2.0 has a more even charge distribution across its surface, a trait it shares with RPTP. In contrast, an entire face of VP1 carries a predominantly negative surface charge.
Figure 6:
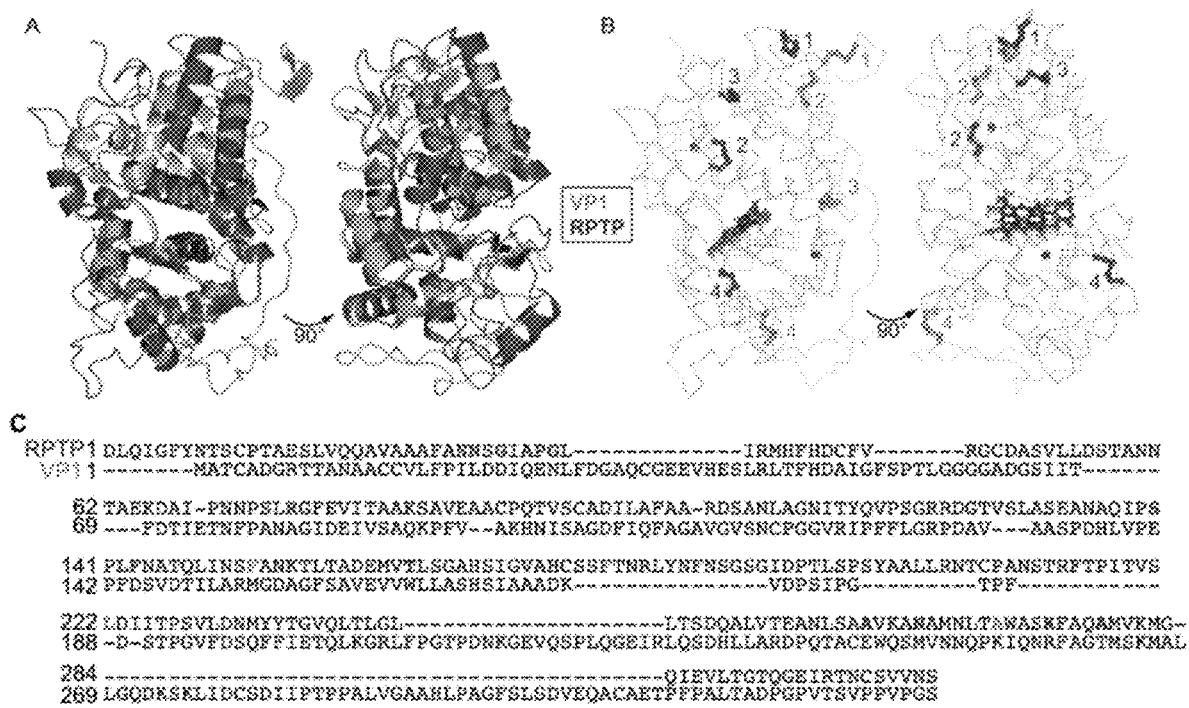
FIG. 6, Panels a-c. Structure and sequence alignment of VP1 and RPTP. Panel a: The crystal structure of VP1 (lighter, Protein Data Bank (PDB) ID: 4BLL) is shown aligned to that of RPTP (darker, PDB ID: 3HDL). The two structures align with a root mean square deviation (RMSD) of 1.76 Å over 209 residues, encompassing the heme coordination pocket and calcium coordination sites. Panel b: The aligned C-alpha traces of VP1 and RPTP are illustrated bound to calcium ions (spheres) and with heme coordinated in their respective heme coordination sites. Disulfide bridges are diagrammed and numbered according to their location within the protein sequence. Heme molecules, calcium ions, and disulfides are colored according to their corresponding structure (VP1, lighter; RPTP, darker). Panel c: The sequence alignment of VP1 (SEQ ID NO:2) and RPTP (SEQ ID NO:1) was generated in T-coffee (1). A total of 16 point mutations were introduced into RPTP to build VP2.0. The mutated residues in RPTP (upper upper sequence) according to the oxidation component to which they belong are: F152, L222, and A270, heme coordination site; S140, L142, and F143, exposed heme edge; T164, A260, N264, K274, A278, LRET pathway; N29, G31, G35, R75, V173 manganese site).

RPTP was chosen as a structural scaffold for VP2.0 because it displays thermal stability on par with that of thermophilic microbial enzymes over a broad pH range (pH 2.8-10.3) (Watanabe et al., supra; Zamorano, et al., *Biochimie* 90(11-12):1737-1749, 2008). VP1 and RPTP share only 18% sequence identity, and further differ in: location of their four disulfide bridges; number of oxidation pathways (3 in VP1 vs. 1 in RPTP); and residue composition of the enzyme surface and heme coordination pocket (FIG. 6). However, VP1 and RPTP share significant structural homology, aligning over 209 residues with an RMSD of 1.76 Å. This alignment encompasses the heme and calcium coordination sites of both enzymes, which greatly facilitated the construction of VP2.0. Sixteen point mutations were introduced into RPTP to complete the oxidation pathways and heme pocket and to minimize any suspected steric hindrances due to the introduction of these new functional residues (FIG. 2 and FIG. 6, panel c). Three mutations (F152M, L222F, A270K) were introduced to complete the heme coordination site of VP2.0 because the key functional residues and overall hydrophobic character of the site were conserved between VP1 and RPTP (Watanabe et al., supra). The exposed heme edge architecture was also conserved between these enzymes, and S140E, L142F, and F143D mutations were introduced into this site to reconstitute the electrostatic and steric environment found in VP1.

Figure 7:
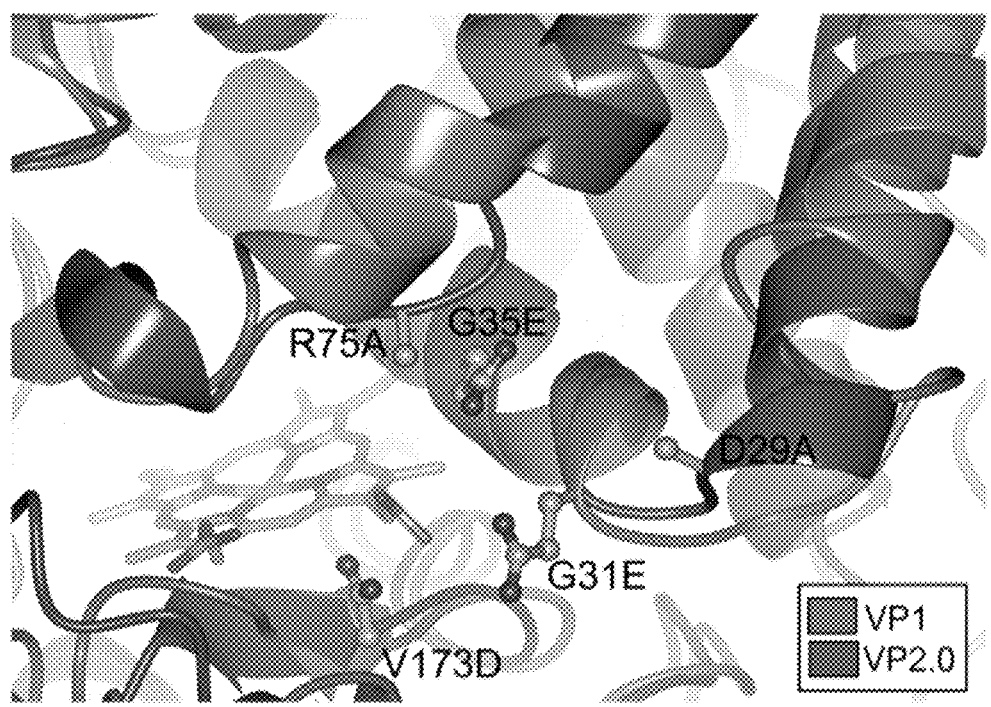
FIG. 7. The design of VP2.0's manganese oxidation site. Although VP2.0 and VP1 align with an RMSD of 1.79 Å over the majority of their structures (210 residues), there are slight structural differences between the two enzymes through their manganese oxidation sites (displayed). RPTP does not contain a manganese oxidation site, so VP2.0's site was created by making the following residue substitutions: D29A, G31E, G35E, R75A, and V173D (labeled). Arg75 sat directly between the heme and potential manganese site and its presence was suspected to hinder heme access, so it was mutated to an alanine to mitigate this possibility. In VP1, this site is formed by two α-helices and a connecting loop, while in VP2.0, this loop is replaced by an extended β-strand. The two glutamates involved in manganese interaction reside on one of the α-helices, and the aspartate sits on the connecting loop in VP1 and on the β-strand in VP2.0. The second α-helix in VP1 extends further over the top of the oxidation site as compared to that of VP2.0, and this combination of increased rigidity at the top and increased flexibility at the bottom of the site might enable VP1 to more productively coordinate manganese, better facilitating oxidation and release. These differences may contribute to VP2.0's decreased manganese oxidation activity as compared to VP1, and construction of a more functional manganese site in VP2.0 may necessitate further engineering of the local secondary and tertiary structure of RPTP.

The LRET pathway and manganese oxidation sites did not exist in RPTP. Therefore, mutations were introduced to construct these sites and account for the residue properties and spatial organization found in VP1. The secondary and tertiary structure of the LRET oxidation pathway location was similar between RPTP and VP1. A surface-exposed tryptophan (T164W) was introduced at the pathway entrance, and a glutamate (A260E), responsible for stabilizing the tryptophan, was placed at hydrogen bond distance to the tryptophan indole nitrogen. Additional mutations (K274R, N264M, A278T) were made to complete the electronic and steric character of this pathway. The manganese oxidation site is the third pathway to be engineered in the creation of VP2.0 and presented further challenges to engineer because VP1 and RPTP differ in residue composition and architecture through this region. This site was constructed in the same location relative to the heme-proprionate group as found in VP1 and special attention to functional residue placement was required to maintain proper geometry for manganese coordination (FIG. 7). In VP1, manganese is coordinated by interactions with three carboxylate groups, and these were introduced with G31E, G35E, and V173D mutations. Glutamate mutations at Gly31 and Gly35 align well with Glu37 and Glu41 in VP1, but placement of the aspartate was more challenging as Asp176 sits on a flexible connecting loop in VP1, while the equivalent position in RPTP is located on a β-strand and placed the aspartate too far from Glu35 (FIG. 7). To maintain similar distances between these residues, aspartate was placed at Val173, 5 Å from Glu35, mimicking the equivalent distance in VP1 (4.2 Å) as closely as possible given the local RPTP structure. Two additional mutations (N29A, R75A) were required to complete this site. RPTP's calcium coordination sites and disulfide bridge locations were preserved in the VP2.0 design.

Example 2. Analysis of Catalytic Versatility and High-Reduction Potential of VP2.0

Figure 3:
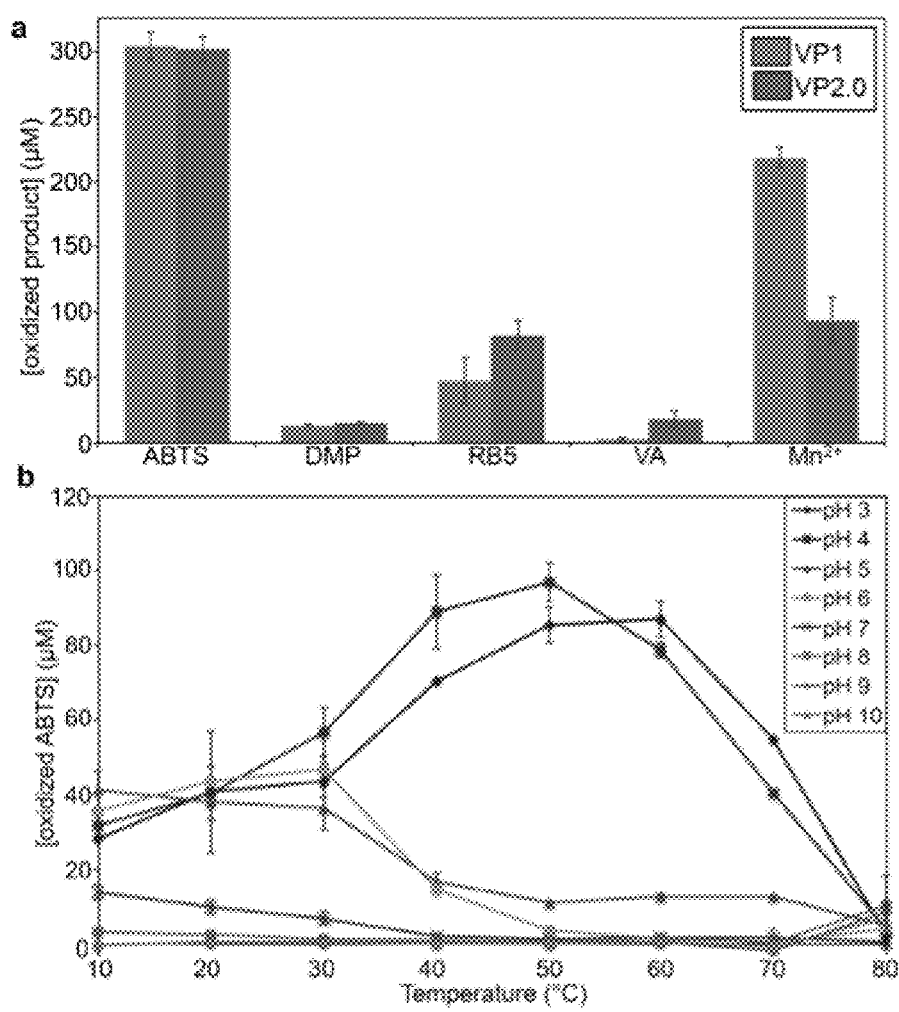
FIG. 3, Panels a-b. VP2.0 exhibits greater oxidative activity on high-reduction potential substrates. Panel a: The activity of VP2.0 (right bars) and VP1 (left bars) was assayed on five standard versatile peroxidase substrates (2,2'-azino-bis(3-ethylbenzothiazoline-6-sulfonic acid (ABTS), 2,6-dimethylphenol (DMP), reactive black 5 (RB5), veratryl alcohol (VA), and manganese ($Mn^{2-}$)). VP2.0 outperformed VP1 on RB5 and VA, but displayed a 60% reduction in activity on $Mn^{2+}$ as compared to VP1. Assays were performed for 2 hours at 30° C. and pH 3 (ABTS, DMP, RB5, VA) and at pH 5 for $Mn^{2+}$. Data presented contain an equivalent enzyme load of 0.25 Units (U), where 1 U is defined as the amount of enzyme required to produce 1 nmol of oxidized ABTS per minute at 30° C. and pH 3. Reactions were performed in triplicate and data shown is mean +/− S.E.M. (black bars). Panel b: The temperature and pH profile of VP2.0-catalyzed ABTS oxidation. Reactions contained 0.04 U of enzyme and were run in duplicate. Data shown is mean +/− S.E.M. (black bars).

To compare the catalytic versatility of VP2.0 with that of its catalytic parent, the ability of each enzyme to oxidize typical VP substrates was evaluated under the optimal conditions reported for VP1 (18) (FIG. 3, panel a). The exposed heme edge traditionally targets low-reduction potential substrates, such as 2,2'-azino-bis(3-ethylbenzothiazoline-6-sulfonic acid (ABTS) and 2,6-dimethylphenol (DMP), and this site functions similarly in VP2.0 and VP1 as both displayed relatively equivalent activity on these substrates (FIG. 3, panel a). Both enzymes exhibited strong oxidation activity on ABTS, generating significantly more oxidized product with ABTS than with any of the other substrates, and both showed similar, though reduced, activity on DMP. Functionality of the high-reduction potential LRET pathway was assessed by measuring the activity of VP2.0 and VP1 on reactive black 5 (RB5), a high-reduction potential dye (18), and veratryl alcohol (VA), a non-phenolic aromatic targeted exclusively by the LRET pathway (23). Although both VP2.0 and VP1 were active on RB5, VP2.0 outperformed VP1 on this substrate, and significantly outperformed VP1 on VA, oxidizing roughly 90% more VA (FIG. 3, panel a).

Because VP2.0's manganese site was the most difficult to engineer, the enzyme's ability to oxidize manganese was of great interest in evaluating the success of its design. To assess VP2.0's manganese oxidation activity, the formation of the manganese (III)-malonate product was measured at the optimal pH for VP1 manganese oxidation (pH 5) (Fernandez-Fueyo et al., 2014, supra; Popp & Kirk, *Arch Biochem Biophys* 288:145-148, 1991). VP2.0 displayed manganese oxidation activity, albeit with approximately 60% lower activity than was measured for VP1 (FIG. 3, panel a). Given the difference in oxidation site architecture between VP1 and RPTP and RPTP's inability to oxidize manganese, it is promising that VP2.0 displayed activity on manganese, and this decreased activity when compared to VP1 may result from imprecise manganese coordination geometry and reduced ability to initially bind or release manganese upon oxidation. In stark contrast to VP2.0, RPTP is only active on low-reduction potential substrates (ABTS and ferulic acid) and is incapable of VA oxidation (Sakharov et al., *Plant Sci* 161:853-860, 2001). Thus, from a catalytic viewpoint, the design of VP2.0 succeeded in reconstructing the key catalytic components of VP1 into the RPTP structural scaffold, producing a peroxidase capable of oxidizing low and high-reduction potential substrates in addition to manganese.

Example 3. VP2.0 Activity Over Broad Temperature and pH Range

Figure 4:
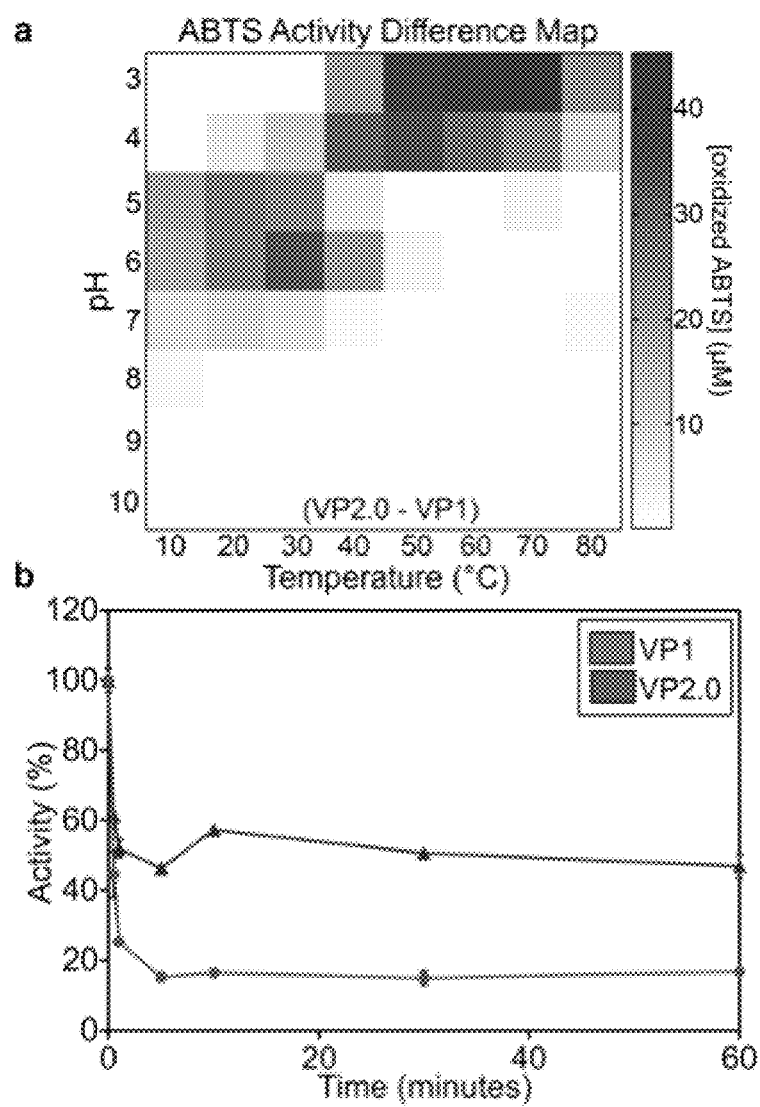
FIG. 4, Panels a-b. VP2.0 outperforms VP1 under extended temperature and pH incubation. Panel a: To assess the effect of temperature and pH stress on enzyme activity, VP2.0 and VP1 were incubated for an hour at temperatures from 10-80° C., in 10° C. steps, and pH from 3-10. ABTS and hydrogen peroxide were then added and the reaction was allowed to proceed. Illustrated here is an activity heat map showing the difference in ABTS oxidation activity between VP2.0 and VP1. Blue areas represent conditions under which VP2.0 outperformed VP1 and degree of blue shading indicates the amount of oxidized ABTS (μM) produced by VP2.0 in excess of that produced by VP1. Experiments were run in triplicate with 0.04 U of enzyme and the resulting temperature and pH profile for each enzyme is presented in FIG. 9. Panel b: The effect of incubation time, or duration of temperature and pH stress, was evaluated by incubating VP2.0 (upper line) and VP1 (lower line) for varying amounts of time and the reaction was then initiated with the addition of ABTS and hydrogen peroxide. The assays contained 0.04 U of enzyme and were run in duplicate. Data shown is the mean +/− S.E.M. (black bars).
Figure 8:
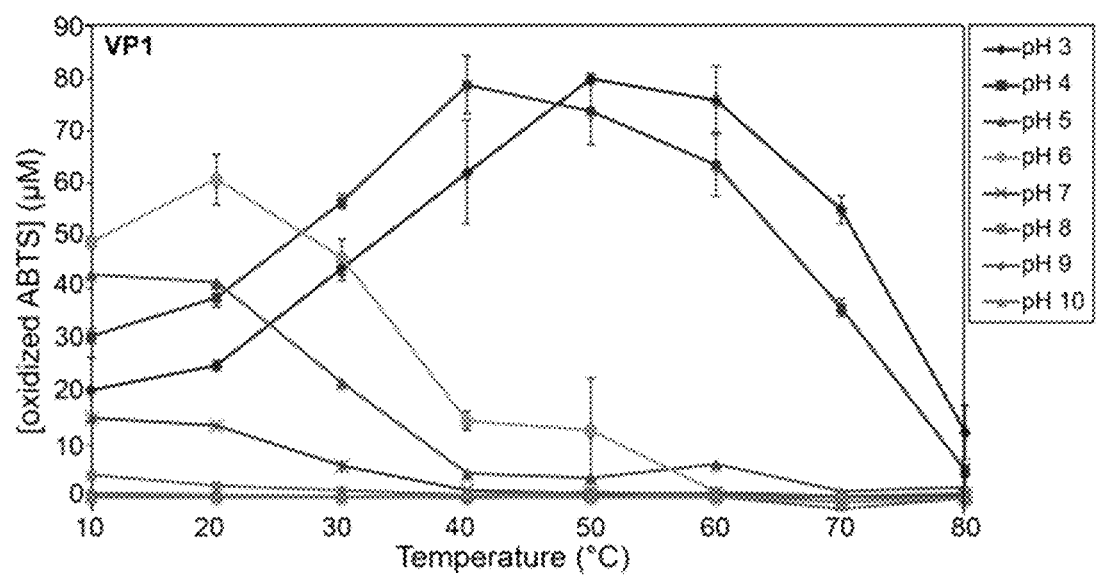
FIG. 8. The activity of VP1 on ABTS. The ability of VP1 to oxidize ABTS was measured at temperatures from 10-80° C., in 10° C. steps, and pH ranging from 3-10. The reactions were run for 2 hours at each condition, and the experiment was performed in duplicate (mean +/− S.E.M. is shown).
Figure 9:
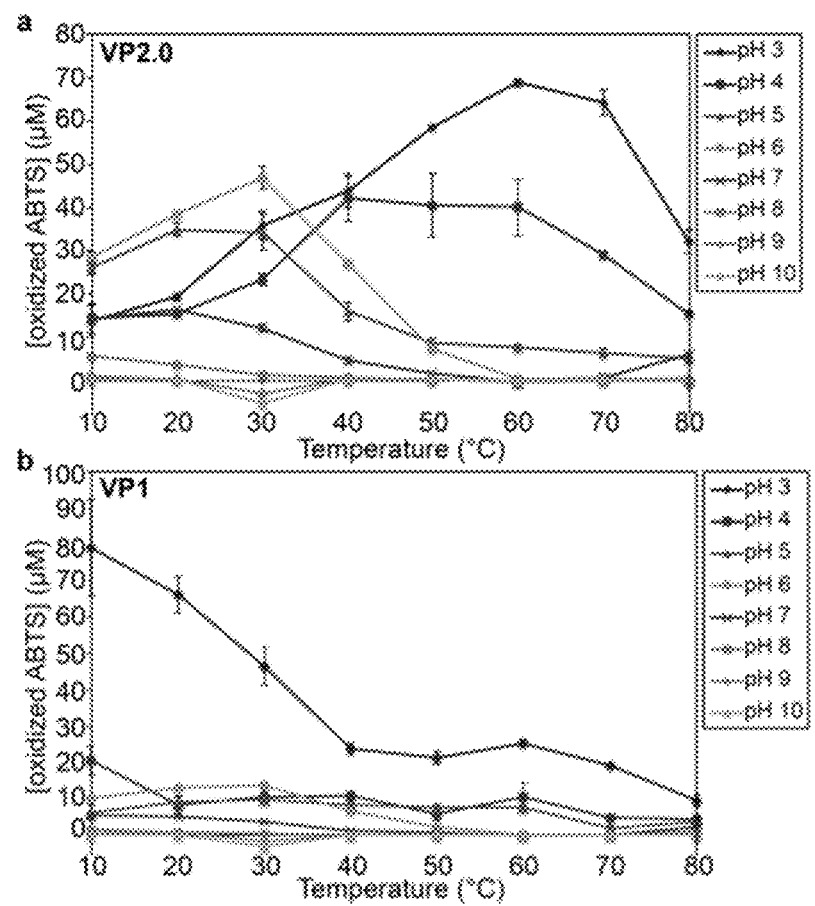
FIG. 9, Panels a-b. The temperature and pH profiles of VP2.0 and VP1 upon temperature and pH stress. VP2.0 (Panel a) and VP1 (Panel b) were subjected to a range of temperature (10-80° C., in 10° C. steps) and pH (3-10) conditions for 1 hour. Reactions were then initiated with the addition of ABTS and hydrogen peroxide and were allowed to proceed. Experiments were run in triplicate and the mean amount of oxidized ABTS produced by each enzyme is plotted with S.E.M. (black bars). The difference in activity between VP2.0 and VP1 (i.e. VP2.0-VP1) is illustrated in Panel a of FIG. 4.

To better understand the conditions necessary for structural stability and fundamental peroxidase activity of VP2.0 and VP1, the ability of these enzymes to oxidize ABTS was assessed over a range of temperature and pH conditions (10-80° C., in 10° C. steps and pH 3-10) (FIG. 3, panel b and FIG. 8). VP2.0 achieved its maximal oxidation activity at pH 3-4 and 40-50° C., and exhibited reduced, but measurable, activity at pH 5-7 and temperatures from 10-30° C. (FIG. 3, panel b and Table 1). The temperature at which the activity of VP2.0 and VP1 dropped to 50% of their maximum ($T_{50,\ activity}$) occurred at 72.2° C. (pH 3) and 68° C. (pH 4) (Table 1). To evaluate structural stability over these temperature and pH ranges, the peroxidases were subjected to a one-hour incubation at each temperature and pH condition described above (FIG. 4, panel a). Under this experimental design, VP2.0 dramatically outperformed its catalytic parent, as its $T_{50,\ activity}$ values were relatively unaltered at its optimal pH (pH 3-4), while VP1's $T_{50,\ activity}$ decreased by 40° C. at pH 3-4 (FIG. 4, panel a and FIG. 9 and Table 1). VP1 exhibited a significant change in its temperature and pH profile upon extended incubation under these conditions. At its optimal pH (pH 3), VP1's optimal temperature shifted dramatically to 10° C., and above pH 4, it was inactive at all assayed temperatures (FIG. 9, panel b). VP2.0 also exhibited a change in its temperature and pH profile with extended incubation, displaying a shift in optimal temperature to 60° C. at pH 3, and reduced activity at pH 4 relative to pH 3 but with no significant change in optimal temperature (FIG. 9, panel a). In contrast to VP1, the activity of VP2.0 was relatively unaffected by incubation at pH 5-7 and temperature from 10-30° C.

VP2.0 decreased over time, this decrease was not as significant as observed for VP1, and VP2.0 maintained a higher residual activity when subjected to increasing stress. Taken together, these results demonstrate VP2.0's enhanced stability and, more importantly for industrial applications, higher activity across broader temperature and pH ranges as compared to its catalytic parent.

VP2.0 Structural Stability Under Optimal VP Reaction Conditions

Figure 5:
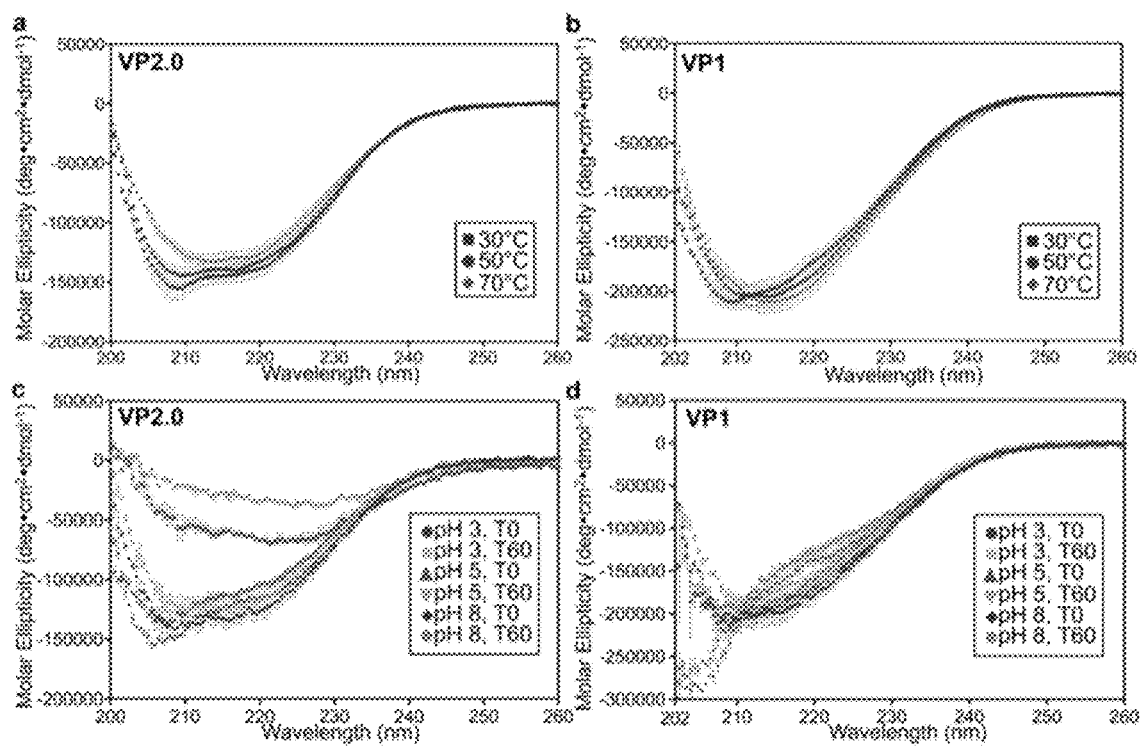
FIG. 5, Panels a-d. The assessment of VP2.0's thermal and pH stability using Far-UV CD spectroscopy provides structural insight into the thermal and pH stability of VP2.0. The effect of temperature on the structural stability of VP2.0 (Panel a) and VP1 (Panel b) was evaluated by measuring the secondary structure spectra of these enzymes using far-UV circular dichroism (CD) spectroscopy at temperatures ranging from 25-80° C. at a constant pH (pH 3). For ease of comparison, data from 30° C., 50° C., and 70° C. is shown here, and the complete data sets can be found in FIG. 10. Both enzymes exhibit far-UV CD spectra characteristic of proteins with high α-helical content. VP2.0 was stable up to 70° C., while VP1 began to display structural instability at 40° C., 30° C. lower than did VP2.0. The effect of pH on the structural stability of VP2.0 (Panel c) and VP1 (Panel d) was also examined using far-UV CD spectroscopy at constant temperature (50° C.) and varied pH (pH 3, 5, 8). Far-UV CD spectra were collected at time 0 (T0) and after 60 minutes (T60) of incubation under these conditions. VP2.0 displayed significant loss of ordered structure at pH 5 but was minimally affected by pH 3 and pH 8. Conversely, VP1 was most stable at pH 5, less stable at pH 3, and experienced a significant conformation change at pH 8. Far-UV CD data was performed in duplicate with 20 μM of enzyme and is presented as mean molar ellipticity +/− S.E.M. (black bars).
Figure 10:
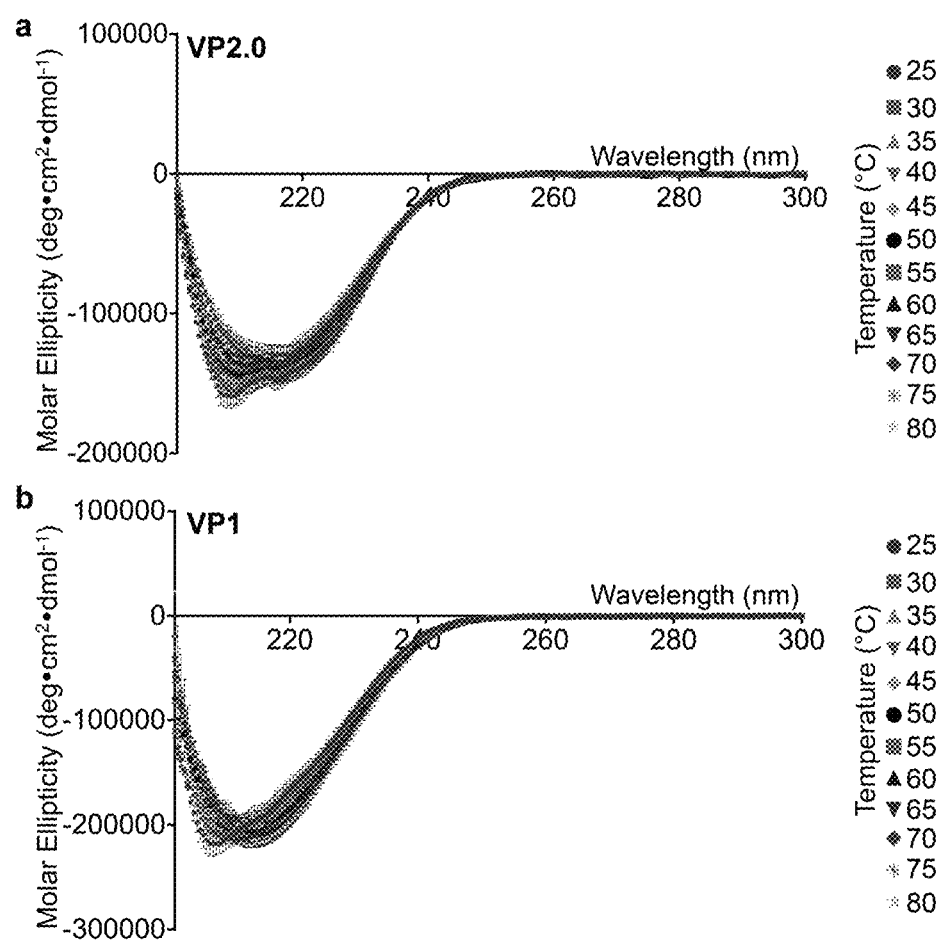
FIG. 10, Panels a-b. The far-UV CD spectra for VP2.0 and VP1 as a function of temperature. To examine the effect of temperature on the structural stability of VP2.0 and VP1, the enzymes were incubated at their optimal pH (pH 3) at temperatures ranging from 25-80° C., in 5° C. steps. Samples were incubated for 1 minute at each temperature step before far-UV CD spectra were collected. The far-UV CD spectra are shown for VP2.0 (Panel a) and for VP1 (Panel b). Spectra were collected in duplicate and plotted as the mean molar ellipticity values +/− S.E.M. (black bars).

VP2.0 and VP1 displayed differing degrees of sensitivity to temperature and pH incubation, and it was hypothesized that one explanation for this difference in sensitivity was due to differences in structural stability between the enzymes. Far-UV circular dichroism (CD) spectroscopy was utilized to investigate the structural stability of these peroxidases by measuring changes in secondary structure upon temperature or pH incubation. The effect of temperature was assessed by incubating each enzyme at their optimal pH (pH 3) at temperatures ranging from 25-80° C. Both peroxidases exhibited far-UV CD spectra characteristic of proteins with high $\alpha$-helical content (24). The far-UV CD spectra of VP2.0 was very similar in profile to that of RPTP (Zamorano et al., supra), suggesting that the overall structural fold of RPTP was indeed conserved in VP2.0. Compared to VP1, VP2.0 had a wider overall trough with double minima at 208 and 222 nm (FIG. 5, panel a). As temperature increased, VP2.0's far-UV CD spectra also displayed similar behavior to that of RPTP, maintaining its characteristic profile from 25-65° C. and the two minima became less defined as temperatures surpassed 70° C. (FIG. 5, panel a and FIG. 10, panel a). Conversely, VP1 displayed a single, distinct minimum at 208 nm at 25° C., and this minimum shifted substantially to the right as temperature increased above 35° C., reaching 215 nm at 80° C. (FIG. 5, panel b and FIG. 10, panel b). Although both enzymes demonstrated a change in secondary structure with increasing temperature, VP2.0 retained its native structure over a wider temperature range than did VP1, resisting secondary structure disruption by 30° C. above the temperature at which VP1 began to exhibit structural change.

The effect of pH on structural stability was evaluated by incubating the enzymes at pH 3, 5, and 8 at their optimal

TABLE 1

Temperature and pH values for VP2.0 and VP1 ABTS activity. $T_{opt}$ and $pH_{opt}$ are the optimal temperature and pH for enzymatic activity, and $T_{50,activity}$ is the temperature at which the enzyme functions at 50% of its maximal activity. The $T_{50,activity}$ values for VP2.0 and VP1 without pre-incubation at pH 3 and pH 4 and with pre-incubation (denoted 'pre-incubated') is provided.

|  | $T_{opt}$ | $pH_{opt}$ | $T_{50,activity}$ (pH 3) | $T_{50,activity}$ (pH 4) | Pre-incubated $T_{50,activity}$ (pH 3) | Pre-incubated $T_{50,activity}$ (pH 4) |
|---|---|---|---|---|---|---|
| VP2.0 | 40-50° C. | pH 3-4 | 72.2° C. +/− 0.4° C. | 68° C. +/− 0.9° C. | 79.3° C. +/− 0.7° C. | 73.6° C. +/− 1.7° C. |
| VP1 | 40-50° C. | pH 3-4 | 73.5° C. +/− 0.1° C. | 68.6° C. +/− 0.9° C. | 33.5° C. +/− 1.1° C. | 33.8° C. +/− 4.4° C. |

Length of incubation, or the amount of time spent under stress, had a substantial effect on the residual activity of VP2.0 and VP1 (FIG. 4, panel b). When these enzymes were incubated for varying lengths of time at their optimal temperature and pH, both displayed a substantial drop in activity over the course of the one-hour experiment. After one minute of incubation, VP1 had lost 75% of its activity, while VP2.0's activity was reduced by 48%, and after one hour, the activity of VP1 had fallen by 83%, whereas VP2.0's activity decreased by 53%. Although the activity of temperature (50° C.), and far-UV CD spectra were collected at time 0 (T0) and after 1 hour (T60) of incubation. At pH 3 and 8, VP2.0 displayed its characteristic, double minima (208, 222 nm) far-UV CD spectra profile (FIG. 5, panel c). VP2.0's minimum at 208 nm was more pronounced at pH 8 as compared to at pH 3, and incubation under these conditions had little effect on the $\alpha$-helical content of VP2.0, as indicated by minimal change in far-UV CD spectra at T0 and T60. At pH 5, VP2.0 demonstrated significant structural instability, which was evident from the large change in its far-UV CD spectra and clear loss of its defined minima (FIG. 5, panel c). Additionally, prolonged incubation at pH 5 led to further secondary structure loss. Interestingly, these structural changes were not substantial enough to render VP2.0 inactive, as the enzyme was still capable of substrate oxidation at pH 5; however, this reduced stability may have contributed to VP2.0's decreased manganese activity (FIG. 3 and FIG. 9, panel a). The far-UV CD spectra of VP1 at pH 3 had a single minimum at 208 nm, and this minimum shifted to 215 nm upon prolonged incubation (FIG. 5, panel d). VP1 was minimally affected by incubation at pH 5, maintaining its minimum (208 nm) with little difference between T0 and T60 spectra. However, VP1 underwent a significant change in far-UV CD spectra at pH 8 (FIG. 5, panel d). Its minimum shifted to 204 nm and its molar ellipticity decreased substantially between 210-225 nm, indicating a shift from predominately α-helical content to random coil motifs (Johnson, *Proteins* 7:205-214, 1990). Although both VP2.0 and VP1 were affected by pH, these analyses indicated that VP2.0 was structurally more stable than its catalytic parent under optimal reaction conditions (pH 3), which is likely a causative factor in VP2.0's ability to outperform VP1 over time.

Summary

VP2.0 shares high sequence homology with RPTP and benefits from many of the structural factors that contribute to RPTP's unusually broad temperature and pH stability, such as a similar inter- and intra-molecular force profile, increased α-helical content, and structural compactness. Alteration of the surface charge distribution and more generally, alteration of residue identity throughout the enzyme, leads to changes in intra-molecular forces, such as salt bridges and hydrogen bonds, that govern secondary structural elements and overall enzyme fold. VP2.0, unlike VP1, has a relatively evenly distributed electrostatic surface potential, which may mitigate self-aggregation and favorably impact its substrate and solvent interactions. VP2.0 has fewer negatively charged surface residues, and thus has an increased pI relative to VP1 (pI(VP2.0)=4.64; pI(VP1)=4.42). Because protein solubility or stability typically decreases as the solution pH approaches the protein pI (Golovanov et al., *J. Am Chem Soc* 126:8933-8939, 2004), this increase in VP2.0's pI would increase its stability at its optimal reaction pH (pH 3-4). As evidenced by far-UV CD spectroscopy, VP2.0 was structurally stable at pH 3, but exhibited a loss of ordered structure when examined at pH 5, closer to its pI.

Disulfide bridges influence the structural stability of globular proteins, and in heme peroxidases, they also influence calcium coordination and enzyme activity. VP2.0 shares RPTP's disulfide bridge pattern, and while the overall number of disulfides is equal between VP2.0 and VP1, the enzymes differ in spatial arrangement of their disulfide bridges (FIG. 6, panel b). The arrangement found in RPTP and VP2.0 is characteristic of secretory plant heme peroxidases, which typically display higher temperature and pH tolerance than do the fungal extracellular heme peroxidases, such as VP1 (Zamorano et al., supra). In particular, RPTP's second disulfide bridge (Cys44-Cys49) restrains an extended loop, which is unrestrained in VP1, and enhances the structural stability of the distal calcium coordination site (Watanabe et al., supra). Calcium coordination is important for heme peroxidase structural stability, as it aids in maintenance of proper heme coordination pocket architecture and influences thermal stability (Saez-Jimenez et al, 2015 and 2016, botj supra). Although the locations and general residue composition of the calcium coordination sites are conserved between VP2.0 and VP1, it is possible that they vary in their ability to coordinate calcium due to differences in organization and strength of nearby intra-molecular interactions, especially if these interactions are variably disrupted by temperature and pH stress. These differences in disulfide bridge arrangement, and possibly calcium coordination, may be important factors in VP2.0's enhanced stability and ability to function over broader ranges of temperature and pH in comparison to VP1.

Finally, VP2.0 is predicted to have longer α-helices, and consequently, 10% greater α-helical content compared to VP1. This increased α-helical content combined with tighter packing of these structural elements, as is observed in RPTP and predicted for VP2.0 (FIG. 6, panel a), may encourage a more rigid overall structure that together with other structural features, like intra-molecular forces and calcium coordination, would enable these enzymes to better withstand harsher conditions. It is important to note that one contributing factor in RPTP stability is the presence of nine N-glycosylation sites (Watanabe et al., supra), and neither VP2.0 nor VP1 are glycosylated when produced recombinantly in *E. coli* BL21(DE3) cells. Nevertheless, as described above, many factors that contribute to RPTP's structural stability are conserved in VP2.0, and although the exact contributions of these factors are difficult to quantify directly, their cumulative, positive effect on VP2.0 is evident in the activity profiling data and far-UV CD spectroscopy results presented here.

Since many structural features have been implicated in heme peroxidase stability, this engineering approach aimed to make substantial, global changes to a VP, combining the positive traits of related but catalytically and species diverse enzymes, to create a high-reduction potential peroxidase that would be amenable to broader industrial application. This example thus demonstrates that the catalytic hardware of VP1 can be rebuilt into a more stable structural scaffold. VP2.0, the resulting peroxidase, displayed greater structural stability than its catalytic parent, and due to this stability, VP2.0 was capable of functionally withstanding extended exposure to a wider range of temperature and pH conditions.

Methodology—Example Section

Gene and Plasmid Construction. Full-length *P. ostreatus* versatile peroxidase (999 bp) (VP1) (GenBank: ALD10061.1) and VP2.0 (915 bp) genes were codon optimized for expression in *Escherichia coli,* synthesized (GenScript), and cloned into the pET-28a(+) expression vector (Novagen-EMD Millipore) between the NheI and NotI restriction sites.

Protein Expression and Purification. The pET-28a(+)-VP2.0 and pET-28a(+)-VP1 vectors were each transformed into *Escherichia coli* BL21(DE3) cells (New England Biolabs, Inc.), and cells were grown in Miller's LB media at 37° C. to an $OD_{600}$ of 0.8-1.0. Protein expression was induced by the addition of 1 mM isopropyl β-D-1-thiogalactopyranoside (IPTG) for 16 hours at 19° C. Cells were harvested by centrifugation (10 minutes at 4,000 rpm), resuspended in 50 mM Tris, pH 8.0, 250 mM sodium chloride, and 0.1 mM phenylmethylsulfonyl fluoride (PMSF), and lysed via homogenization. The homogenized cell mixture was centrifuged (40 minutes at 10,000 rpm) to separate soluble protein material from membrane-associated protein material. The soluble protein material (supernatant) was discarded and the membrane-associated material (pellet) was resuspended in 50 mM Tris, pH 8.0, 250 mM sodium chloride, 5 mM imidazole, and 8 M urea. The solubilized material was centrifuged to remove any remaining cell debris (40 minutes at 10,000 rpm), and the resulting supernatant was applied to Ni-NTA resin (Qiagen) at room temperature (approximately 22° C.). The protein was eluted from the resin in 50 mM Tris, pH 8.0, 250 mM sodium chloride, 500 mM imidazole, and 8 M urea.

The denatured, purified VP2.0 and VP1 proteins were refolded in vitro using a dialysis refolding method modified from that described by Perez-Boada, et al., *Enzyme and Microbial Technology* 30:7, 2002). Dialysis was performed at room temperature, in the dark, with gentle stirring for approximately 20 hours. The dialysis buffer contained: 5 mM calcium chloride, 0.5 mM oxidized glutathione, 0.1 mM 1,4-dithiothreitol, 0.16 M urea, 20 µM hemin, and 20 mM Tris, pH 9.5. Both proteins were diluted using the dialysis buffer to a concentration of 0.1-0.2 mg/mL prior to refolding and the ratio of protein volume to dialysis buffer volume was maintained at a 1:18 ratio. Post-dialysis, refolded VP2.0 and VP1 were loaded directly onto a HiTrap Q HP anion exchange column (GE Healthcare) that was equilibrated in 10 mM sodium tartrate, pH 5.5 and 1 mM calcium chloride at a 1 mL/minute load rate. Protein was eluted from the column using a sodium chloride gradient from 0-1 M run at 2 mL/min over 60 minutes. Both VP2.0 and VP1 eluted from the anion exchange column at a sodium chloride concentration of approximately 400-500 mM. As a final purification step, VP2.0 and VP1 were purified by size-exclusion chromatography using a Superdex 200 HiLoad 16/600 column (GE Healthcare) into a final buffer of 10 mM sodium tartrate, pH 5.5, 200 mM sodium chloride, 1 mM calcium chloride. Protein was flash-frozen and stored at −80° C.

Substrate Screen Assay. For all enzymatic assays with VP2.0 and VP1, Units (U) are defined as the amount of enzyme that produces 1 nmol of oxidized 2,2'-azino-bis(3-ethylbenzothiazoline-6-sulphonic acid (ABTS) per minute at 30° C. and pH 3. To assess the ability of VP2.0 and VP1 to oxidize substrates of varying redox potential, each enzyme was incubated with either ABTS, Reactive Black 5 (RB5), 2,6-dimethylphenol (DMP), veratryl alcohol (VA), or manganese for 2 hours at 30° C. To measure enzyme activity on ABTS and DMP each reaction contained 0.06 U of enzyme, 5 mM hydrogen peroxide, 1 mM substrate (ABTS or DMP), and 50 mM sodium tartrate, pH 3. To determine enzyme activity on RB5, reactions contained 0.06 U of enzyme, 0.2 mM RB5, and 5 mM hydrogen peroxide, and 50 mM sodium tartrate, pH 3. For VA oxidation, reactions contained 0.25 U of enzyme, 1 mM VA, 5 mM hydrogen peroxide, and 50 mM sodium tartrate, pH 3. ABTS, DMP, RB5, and VA assays were adapted from protocols described by Fernandez-Fueyo, et al., supra. A protocol similar to that described by Popp, et al., *Arch Biochem Biophys* 288:145-148, 1991 was used to assess enzyme activity on manganese, and the reaction contained 0.25 Units of VP2.0 or VP1, 20 mM sodium malonate, pH 5, 10 mM manganese sulfate, and 1 mM hydrogen peroxidase. The formation of the oxidized product was determined for each reaction by measuring the change in absorbance at the following wavelengths (product measured in parentheses): 436 nm (ABTS cation radical), 598 nm (disappearance of RB5), 469 nm (dimeric coerulignone), 310 nm (veratraldehyde), 266 nm (formation of Mn(III)-malonate complex) (18, 25). Background absorbance due to the enzyme, buffer, and substrates was subtracted from the raw absorbances, and product concentrations were calculated from the resulting absorbance values using the following molar extinction coefficients: $\varepsilon_{436}$=29.3 mM$^{31\ 1}$ cm$^{-1}$, $\varepsilon_{598}$=30 mM$^{-1}$ cm$^{-1}$, $\varepsilon_{469}$=55 mM$^{-1}$ cm$^{-1}$, $\varepsilon_{310}$=9.3 mM$^{-1}$ $\varepsilon_{266}$=11.5 mM$^{-1}$ cm$^{-1}$ (18, 25). Enzyme reactions were run in triplicate, and data presented in FIG. 3, panel a are adjusted for an equivalent enzyme load of 0.25 U for activity comparison across substrates. All spectroscopic assays were performed on a SpectraMax Plus 384 spectrophotometer (Molecular Devices, Sunnyvale, Calif.).

Temperature and pH Assays. The temperature and pH profiles for VP and VP2.0 were determined by measuring the ability of each enzyme to catalyze oxidization of ABTS under temperatures ranging from 10° C. to 80° C. (measured in 10° C. increments) and pH ranging from pH 3-10 (measured in 1 pH unit steps). Each reaction contained 0.04 U of either VP1 or VP2.0, 1 mM calcium chloride, 1 mM ABTS, 5 mM hydrogen peroxide, 50 mM buffer agent. The buffering agents included: citric acid pH 3 and 4, sodium malonate pH 5, citric acid pH 6, tris(hydroxymethyl)aminomethane (Tris) pH 7 and 8, and N-cyclohexyl-2-aminoethanesulfonic acid (CHES) pH 9 and 10. Reactions were incubated for 2 hours and the concentration of oxidized ABTS was determined from the sample absorbance collected at 436 nm. Temperature and pH profile assays were performed in duplicate. For the temperature and pH pre-incubation experiment, 0.04 Units of VP1 or VP2.0 in 1 mM calcium chloride, and 50 mM buffering agent (described above) were incubated at 10° C. to 80° C. (in 10° C. steps) for 1 hour. 1 mM ABTS and 5 mM hydrogen peroxide was then added to each reaction and the samples were incubated again at their respective temperatures for another hour. The concentration of oxidized ABTS was determined as described above. For both experiments, the background absorbance due to enzyme, buffer, and substrates was subtracted from the raw absorbances, and concentration of oxidized ABTS was determined from the molar extinction coefficient: $\varepsilon_{436}$=29.3 mM$^{-1}$ cm$^{-1}$. The temperature and pH pre-incubation assay was performed in triplicate.

For the time course experiment, 0.06 Units of VP2.0 and VP1 were incubated in 50 mM citric acid pH 3 at 50° C. and time point aliquots were taken after 0, 0.5, 1, 5, 10, 30, and 60 minutes of incubation at 50° C. Time point reactions were initiated upon addition of 1 mM ABTS and 5 mM hydrogen peroxide, and reactions were allowed to proceed at 50° C. for 1 hour. The concentration of oxidized ABTS was determined as detailed for the temperature and pH profile experiment, and the background absorbance due to the presence of enzyme, buffer, and substrates was subtracted from the raw absorbance values. Experiments were run in duplicate.

Circular Dichroism Spectroscopy. Circular dichroism (CD) spectra were acquired with a Jasco J-815 spectropolarimeter (JASCO, Maryland, USA) that was equipped with a Peltier temperature controller. For the temperature interval spectra, each sample contained 20 µM of enzyme prepared in 10 mM citric acid buffer (pH 3). Scans were performed in a 1 mm path length cell from 300 to 190 nm with a data pitch of 0.5 nm and a 1 nm bandwidth. The temperature was varied from 25° C. to 80° C., in 5° C. intervals, and samples were incubated at each temperature for 60 seconds before data collection. This delay in data acquisition was based on the time course findings that the majority of activity loss occurred within a one-minute incubation, thus measurements were expected to reflect structural changes, if present. The scanning speed was 50 nm/minute with a ramp rate of 40° C./hour. Scans were performed in duplicate for each enzyme and pH. The spectra for the buffer alone (10 mM citric acid pH 3) was subtracted from the sample spectra and the resulting data was smoothed using the Jasco Spectra Manager v.2 software (JASCO, Easton, Md.). Raw ellipticity ($\theta_{obs}$) values were converted to mean residue ellipticity ($\theta_{molar}$) using equation (1):

$$\vartheta_{molar}=100*\vartheta_{obs}/m*d \qquad (1)$$

where m is molar enzyme concentration (M) and d is the path length of the cell (cm). Spectra data was plotted as the mean with standard error of the mean (S.E.M.) in Prism 7.0a (GraphPad Software, Inc., La Jolla, Calif.) (Kelly et al., *Biochim Biophs Acta* 1751:119-139, 2005).

For pH screen spectra, each sample contained 20 μM of enzyme prepared in different buffers: 10 mM citric acid pH 3, 10 mM sodium malonate pH 5, and 10 mM Tris pH 8. Scans were performed in a 1 mm path length cell from 300 to 190 nm with a data pitch of 0.5 nm and a 1 nm bandwidth. The scanning speed with 50 nm/minute and the temperature was held constant at 50° C. Spectra were collected before incubation at 50° C. (Time 0) and after 1 hour of incubation at 50° C. (Time 60 minutes). The spectra for each buffer was subtracted from the corresponding sample spectra and raw ellipticity values were converted to molar ellipticity using equation (1). Spectra for each enzyme and pH were collected in duplicate.

Although the foregoing invention has been described in some detail by way of illustration and example for purposes of clarity of understanding, one of skill in the art will appreciate that certain changes and modifications may be practiced within the scope of the appended claims. In addition, each publication and accession number provided herein is incorporated by reference in its entirety to the same extent as if each reference was individually incorporated by reference. Where a conflict exists between the instant application and a reference provided herein, the instant application shall dominate.

---

Illustrative sequences

---

SEQ ID NO: 1 *Roystonea regia* peroxidase amino
acid sequence
DLQIGFYNTSCPTAESLVQQAVAAAFANNSGIAPGLIRMHFHDCFVRGCD
ASVLLDSTANNTAEKDAIPNNPSLRGFEVITAAKSAVEAACPQTVSCADI
LAFAARDSANLAGNITYQVPSGRRDGTVSLASEANAQIPSPLFNATQLIN
SFANKTLTADEMVTLSGAHSIGVAHCSSFTNRLYNFNSGSGIDPTLSPSY
AALLRNTCPANSTRFTPITVSLDIITPSVLDNMYYTGVQLTLGLLTSDQA
LVTEANLSAAVKANAMNLTAWASKFAQAMVKMGQIEVLTGTQGEIRTNCS
VVNS SEQ ID NO: 2 *Pleurotus ostreatus* VP1 amino acid
sequence
MATCADGRTTANAACCVLFPILDDIQENLFDGAQCGEEVHESLRLTFHDA
IGFSPTLGGGGADGSIITFDTIETNFPANAGIDEIVSAQKPFVAKHNISA
GDFIQFAGAVGVSNCPGGVRIPFFLGRPDAVAASPDHLVPEPFDSVDTIL
ARMGDAGFSAVEVVWLLASHSIAAADKVDPSIPGTPFDSTPGVFDSQFFI
ETQLKGRLFPGTPDNKGEVQSPLQGEIRLQSDHLLARDPQTACEWQSMVN
NQPKIQNRFAGTMSKMALLGQDKSKLIDCSDIIPTPPALVGAAHLPAGFS
LSDVEQACAETPFFPALTADPGPVTSVPPVPGS SEQ ID NO: 3 Engineered hybrid peroxidase amino
acid sequence
DLQIGFYNTSCPTAESLVQQAVAAAFANASEIAPELIRMHFHDCFVRGCD
ASVLLDSTANNTAEKDAIPNNPSLAGFEVITAAKSAVEAACPQTVSCADI
LAFAARDSANLAGNITYQVPSGRRDGTVSLASEANAQIPEPFDNATQLIN
SMANKTLTADEMVWLSGAHSIGDAHCSSFTNRLYNFNSGSGIDPTLSPSY
AALLRNTCPANSTRFTPITVSFDIITPSVLDNMYYTGVQLTLGLLTSDQA
LVTEANLSAEVKAMAMNLTKWASRFAQTMVKMGQIEVLTGTQGEIRTNCS
VVNS SEQ ID NO: 4 tag amino acid sequence (used to
produced and purify the target protein *Pleurotus
ostreatus* VP1 as described in the EXAMPLES
section).
MGSSHHHHHHSSGLVPRGSHMAS SEQ ID NO: 5 4USC_A, *Chamaerops excelsa* peroxidase
amino acid sequence
DLQIGFYNQSCPSAESLVQQGVAAAFANNSGIAPGLIRMHFHDCFVRGCD
GSVLLDSTDINTAEKDAAPNNPSLRGFEVIAAAKSAVEAACPKTVSCADI
LAFAARDSAALAGNITYQVPSGRRDGNVSLASEALTNIPAPTFNATQLIN
SFAGKNLTADEMVTLSGAHSIGVSHCFSFLNRIYNFSNTSQVDPTLSSSY
ADLLRTKCPSNSTRFTPITVSLDIITPTVLDNRYYTGVQLTLGLLTSDQA
LVTEANLSAAVKNNADNLTATATVAEFAQAIVKMGQIEVLIGTQGEIRTN
CSVVN SEQ ID NO: 6 A5B30702.1, *Elaeis guieensis*
peroxidase amino acid sequence
DLQIGFYNTSCPTAESLVQQAVAAAFANNSGIAAGLIRLHFHDCFVRGCD
ASVLLDSTANNTAEKDAPPNNPSLRGFEVIAAAKSAVEAACPKTVSCADI
VAFAARDSATLAGNISYQVPSGRRDGNVSLASEANANIPSPLFNATQLIN
SFAGKNLTTDEMVTLSGAHSIGVAHCSSFLNRIYNFSNTSDVDPTLSSAY
ADLLKNKCPSNSTRFTPITVSLDIITPTVLDNRYYTGVELTLGLLTSDQA
LVTEANLSAAVQDNANNSATTNASKFAQAMVKMGLIEVLIGTQGEIRTNC
SVVNSAS SEQ ID NO: 7 AIX03725.1, *Trachycarpus fortunei*
peroxidase amino acid sequence
MSRPVKLFFLAFLALLAAVHGDLQIGFYNQSCPSAESLVQQAVAAAFANN
SGIAPGLIRMHFHDCFVRGCDASVLLDSTANNTAEKDAAPNNPSLRGFEV
IAAAKSAVEAACPKTVSCADILAFAARDSAALAGNITYQVPSGRRDGNVS
LASEALTNIPAPTFNATQLINSFAGKNLTADEMVTLSGAHSIGVSHCFSF
LNRIYNFSNTSQVDPTLSSSYADLLRTKCPSNSTRFTPITVSLDIITPTV
LDNRYYTGVQLTLGLLTSDQALVTEANLSAAVKNNADNLTAWVAKFAQAI
VKMGQIQVLIGTQGEIRTNCSVVNSASLGDIVMASGHLTEVATS SEQ ID NO: 8 XP_008810078.1, *Phoenix dactylifera*
peroxidase amino acid sequence
MHLQGCDASVLLNSTANNTAERDAAPNNPSLRGFEVIDAAKSAVEAACPQ
TVSCADILAFAARDSANLTGNITYQVPSGRRDGTVSLASEALANIPAPTF
NATQLINSFANKSLTADEMVTLSGAHSIGISHCASFLNRIYNFSNTSDVD
PTLSSAYADLLKAKCPANSTRFTPITASLDIITPAVLDNMYYTGVQLTLG
LLTSDQALVTQANLSAAVNNNANNLTATNASKFALAMVKMGQIQVLIGTQ
GEIRTNCSVVNSGGLGYVGMGSGHPSEVATS SEQ ID NO: 9 XP_020588657.1, *Phalaenopsis
equestris* peroxidase amino acid sequence
MLSLMKQILFLFLLAVAVAPPPAVNGQLKIGFYNQTCPSAESVVQKTVAA
ASANNTGILAGLIRLFFHDCFVRGCDSSVLLDSTANNTAEKDAPPNHPSL
RGFEVIDAAKSAVEAICPNTVSPTTAPCADIVAFAARDAAALSGNISYQI
PSGRRDGNISLASDANANLPSPLSNASTLITAFAAKNLTADELVTLSGAH
SIGVSHCSSFRNRLYNFSSSSQGDPTLNPAYAALLRFACPFNSTSSGNTT
VAMDVLTPVVLDNFYYIGLKMSLGLFTSDHALLTQGNLSAAVDDNATNNP
AGTNAAKFARAMVKMGSIQVKTGTQGEIRRNCRVVNGRSLANVGPAAEEQ
GSSLVADM SEQ ID NO: 10 XP_020114352.1, *Ananas comosus*
peroxidase amino acid sequence
MVSIKYCRRSLVQVVKYLLGCDGSVLIDSTANNTAEKDAIPNNPSLHGFE
VIDAAKSVVEAQCPETVSCADILAFAARDSITLTGNVTYQVPAGRRDGTV
SNASEVIPNIPAPTFNSTQLINSFQAKNLTAEEMVILSGAHTVGVSHCSS
FLNRIYNFSNTSQVDPTMSPAYAKLLQALCPSNSTRFTPITTGLDVISPG
VLDNKYYVGLTNSLSLLTSDHALLTDANLSAAVSRFATHQSATNESKFTK
AMVRMGEIQVLTGTEGQIRLNCRVVNNASTTAAAAAATGFGSVVGSSHYT
AGGVATI

What is claimed is:

1. A variant heme peroxidase that oxidizes manganese and high-reduction potential substrates at a temperature of 70° C., wherein the variant heme peroxidase has at least 85% identity to SEQ ID NO:3, and comprises at least ten amino acid substitutions, relative to a native thermal-stable heme peroxidase polypeptide comprising sequence SEQ ID NO:1, at positions corresponding to positions 152, 222, 270, 140, 142, 143, 260, 164, 274, 264, 278, 31, 35, 173, 29, and 75 of SEQ ID NO:1, wherein the at leat 10 substitutions are selected from the following: an aromatic amino acid at position 222, 142, or 164; a non-polar amino acid at positoin 152, 264, 29, or 75; a basic amino acid at position 270 or 274; and an acidic amino acid at position 140, 143, 260, 31, 35, or 173.

2. The variant heme peroxidase of claim 1, comprising substitutions, relative to the native thermal-stable heme peroxidase polypeptide sequence, at fifteen positions, or at each position corresponding to positions 152, 222, 270, 140, 142, 143, 260, 164, 274, 264, 278, 31, 35, 173, 29, and 75 of SEQ ID NO:1.

3. The variant heme peroxidase of claim 1, wherein the substitutions are selected from the group consisting of 152M, 222F, 270K, 140E, 142F, 143D, 260E, 164W, 274R, 264M, 278T, 31E, 35E, 173D, 29A, and 75A.

4. The variant heme peroxidase of claim 1, comprising an aromatic amino acid sequence at position 222, 142, 164; a non-polar amino acid substitutions at positions 152, 264, 29, or 75; a basic amino acid at position 270 and 274; and an acidic amino acid at position 140, 143, 260, 31, 35, and 173.

5. The variant heme peroxidase of claim 4, wherein the amino acid sequence has at least 90% identity to SEQ ID NO:3.

6. The variant heme peroxidase of claim 1, wherein the amino acid sequence has at least 95% identity to SEQ ID NO:3.

7. The variant heme peroxidase of claim 1, comprising the amino acid sequence of SEQ ID NO:3.

8. An isolated nucleic acid encoding a variant heme peroxidase of claim 1.

9. A vector comprising the nucleic acid of claim 8.

10. A host cell comprising the nucleic acid of claim 8.

11. The host cell of claim 9, wherein the host cell is a bacteria, cyanobacteria, yeast, or filamentous fungus.

12. A method of oxidizing an aromatic peroxidase substrate or manganese, the method comprising incubating a reaction mixture comprising the substrate and the variant heme peroxidase of claim 1 under conditions in which the peroxidase is catalytically active.

13. The method of claim 12, wherein the substrate comprises manganese.

* * * * *

UNITED STATES PATENT AND TRADEMARK OFFICE
CERTIFICATE OF CORRECTION

| | | |
|---|---|---|
| PATENT NO. | : 10,696,954 B2 | Page 1 of 1 |
| APPLICATION NO. | : 16/215479 | |
| DATED | : June 30, 2020 | |
| INVENTOR(S) | : Amanda C. Kohler et al. | |

It is certified that error appears in the above-identified patent and that said Letters Patent is hereby corrected as shown below:

In the Claims

In Column 47, Line 23, Claim 1, delete "positoin" and replace with --position--

Signed and Sealed this
Seventeenth Day of September, 2024

*Katherine Kelly Vidal*

Katherine Kelly Vidal
*Director of the United States Patent and Trademark Office*